(12) United States Patent
Scholl et al.

(10) Patent No.: US 7,250,497 B2
(45) Date of Patent: Jul. 31, 2007

(54) LARGE DELETIONS IN HUMAN BRCA1 GENE AND USE THEREOF

(75) Inventors: Thomas Scholl, Salt Lake City, UT (US); Brant C. Hendrickson, Salt Lake City, UT (US); Benjamin Ward, Park City, UT (US); Dmitry Pruss, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 590 days.

(21) Appl. No.: 10/457,839

(22) Filed: Jun. 9, 2003

(65) Prior Publication Data

US 2004/0014115 A1   Jan. 22, 2004

Related U.S. Application Data

(60) Provisional application No. 60/387,132, filed on Jun. 7, 2002, provisional application No. 60/402,430, filed on Aug. 9, 2002.

(51) Int. Cl.
C07H 21/02  (2006.01)
C12P 19/34  (2006.01)

(52) U.S. Cl. ..................... 536/23.1; 435/91.2
(58) Field of Classification Search ................ 536/23.1
See application file for complete search history.

(56) References Cited

U.S. PATENT DOCUMENTS

| | | | |
|---|---|---|---|
| 5,622,829 A | 4/1997 | King et al. | |
| 5,821,328 A | 10/1998 | King et al. | |
| 6,150,514 A | 11/2000 | Swensen | |
| 6,512,091 B1 | 1/2003 | King et al. | |
| 2002/0198371 A1* | 12/2002 | Wang | ........................ 536/24.3 |

FOREIGN PATENT DOCUMENTS

WO    WO 98/55650    12/1998

OTHER PUBLICATIONS

Brown, Melissa A. et al., "Germline *BRCA1* Promoter Deletions in UK and Australian Familial Breast Cancer Patients: Identification of a Novel Deletion Consistent With *BRCA1*:ψ *BRCA1* Recombination", *Human Mutation*, 2002; 19:435-442.
Duponchel, Christiane et al., "Rapid Detection by Fluorescent Multiplex PCR of Exon Deletions and Duplications in the *C1 Inhibitor* Gene of Hereditary Angioedema Patients", *Human Mutation*, 2001; 17:61-70.
Gad, Sophie et al., "Color Bar Coding the *BRCA1* Gene on Combed DNA: A Useful Strategy for Detecting Large Gene Rearrangements", *Genes, Chromosomes & Cancer*, 2001; 31:75-84.
Huber, L. Julie et al., "Impaired DNA Damage Response in Cells Expressing an Exon 11-Deleted Murine Brca1 Variant That Localizes to Nuclear Foci", *Molecular And Cellular Biology*, Jun. 2001; 21(12):4005-4015.
Jakubowska, A. et al., "Detection of Germline mutations in the BRCA1 gene by RNA-based sequencing", *Human Mutation*, Aug. 2001; 18(2):149-156.
Montagna, Marco et al., "Identification of a 3 kb Alu-mediated *BRCA1* gene rearrangement in two breast/ovarian cancer families", *Oncogene*, 1999; 18:4160-4165.
Niederacher, Dieter et al., "Patterns of Allelic Loss on Chromosome 17 in Sporadic Breast Carcinomas Detected by Fluorescent-Labeled Microsatellite Analysis", *Genes, Chromosomes & Cancer*, 1997; 18:181-192.
Ostrow, K.L. et al., "A *BRCA1* variant, IVS23+1G→A, causes abnormal RNA splicing by deleting exon 23", *Cancer Genetics and Cytogenetics*, 2001; 127:188-190.
Payne, Shannon R. et al., "Complex Germline Rearrangement of *BRCA1* Associated with Breast and Ovarian Cancer", *Genes, Chromosomes & Cancer*, 2000; 29:58-62.
Petrij-Bosch, Anne et al., "*BRCA1* genomic deletions are major founder mutations in Dutch breast cancer patients", *Nature Genetics*, Nov. 1997; 17:341-345.
Puget, Nadine et al., "A 1-kb Alu-mediated Germ-Line Deletion Removing *BRCA1* Exon 17", *Cancer Research*, Mar. 1, 1997; 57:828-831.
Puget, Nadine et al., "An *Alu*-Mediated 6-kb Duplication in the *BRCA1* Gene: A New Founder Mutation?", *Am. J. Hum. Genet.*, 1999; 64:300-302.
Puget, Nadine et al., "Screening for Germ-Line Rearrangements and Regulatory Mutations in *BRCA1* Led to the Identification of Four New Deletions", *Cancer Research*, Jan. 15, 1999; 59:455-461.
Puget, Nadine et al., "Distinct *BRCA1* Rearrangements Involving the *BRCA1*Pseudogene Suggest the Existence of a Recombination Hot Spot", *Am. J. Hum. Genet.*, 2002; 70:858-865.
Rohlfs, Elizabeth M. et al., "An *Alu*-Mediated 7.1 kb Deletion of *BRCA1* Exons 8 and 9 in Breast and Ovarian Cancer Families That Results in Alternative Splicing of Exon 10", *Genes, Chromosomes & Cancer*, 2000; 28:300-307.
Rohlfs, Elizabeth M. et al., "In-frame deletions of *BRCA1* may define critical funtional domains", *Hum. Genet.*, 2002; 107:385-390.
Smith, Todd M. et al., "Complete Genomic Sequence and Analysis of 117 kb of Human DNA Containing the Gene *BRCA1*", 1996; 6:1029-1049.
Swensen, Jeff et al., "Identification of a 14 kb deletion involving the promoter region of *BRCA1* in breast cancer family", *Human Molecular Genetics*, 1997; 6(9):1513-1517.
Thakur, Sanjay et al., "Localization of BRCA1 and a Splice Variant Identifies the Nuclear Localization Signal", *Molecular And Cellular Biology*, Jan. 1997; 17(1):444-452.
Wilson, Cindy A. et al., "Differential subcellular localization, expression and biological toxicity of BRCA1 and the splice variant BRCA1-Δ11b", *Oncogene*, 1997; 14:1-16.
Xu, Xiaoling et al., "Centrosome Amplification and a Defective $G_2$-M Cell Cycle Checkpoint Induce Genetic Instability in BRCA1 Exon 11 Isoform-Deficient Cells", *Molecular Cell*, Mar. 1999; 3:389-395.

* cited by examiner

*Primary Examiner*—Shanon Foley
*Assistant Examiner*—Sean E Aeder
(74) *Attorney, Agent, or Firm*—Herbert L. Ley, III; Jay Z. Zhang; Myriad IP Department

(57) ABSTRACT

Large deletions have been identified in the BRCA1 gene in patients. The large deletions predispose the patients to breast cancer and ovarian cancer. Thus, methods for detecting the genetic variants are provided which can be used in detecting a predisposition to cancer.

20 Claims, 9 Drawing Sheets

UPSTREAM 56,950 ATCCACCCGTCTCGGCCTCCCAAAGTGCTGGGATTACAGGTGTGAGCCACCGTGCTCGG
               |||||||||     |||||||||||||||||||||||||||||||||||||
        63,286 ATCCACCTACCTCGGCCTCCCAAAGTGCTGGGATTACAGGTGTGAGCCATCGCGGCCTAG DOWNSTREAM

DELETION LOCUS: ATCCACCCGTCTCGGCCTCCCAAAGTGCTGGGATTACAGGTGTGAGCCATCGCGGCCTAG

FIGURE 1

```
UPSTREAM    54,940  ACAGAGCAAGACTCCATCT-CAAAAATATATATATATATATATACA
                                          | |   | ||||||| ||| ||
            62,123                        GGTAAAACCCAGTCTCTACTAAAATACATAAATTGGCTGGGCGTG  DOWNSTREAM

DELETION LOCUS:     ACAGAGCAAGACTCCATCTCAAAAAAATACATAAATTGGCTGGGCGT
```

FIGURE 2

```
UPSTREAM    55,883  GCTTACGCCCTGTAATCCCAGCACTTTGGGAGGCCGAGATCACCTGAGGGCAGGA
                           ||| ||||||||||||||||||| ||||||| |||||||| ||  ||||||||
            62,039  GCTCGCATCAGTAATCCCAGCACTTTGGGAGCCTGAGGGCAGATCACA--AGGTCAGGA  DOWNSTREAM

DELETION LOCUS:     GCTTACGCCCTGTAATCCCAGCACTTTGGGAGGCCCGAGGCCGGAGATCACAAGGTCAGGA
```

FIGURE 3

```
UPSTREAM    56,070   AACCTGGGAGGCAGAGAGGTTTCAGTGAGCTGAGAGATCGGCGCCATTGCA
                     |||  |||||  |||||||| ||||| ||   |||||| ||| ||||||
            61,818   AACCCAGGAGGTGGAGGTTGCAGTGACCCAAGATCGCACCATTGCA  DOWNSTREAM

DELETION LOCUS:      AACCTGGGAGGCAGAGAGGTTTCAGTGACCCAAGATCGCACCATTGCA
```

FIGURE 4

UPSTREAM 53,020 CAGGTGCCTGTAATCCCAGCTACTCAGGAGGCTGAGGCAGGAGAATTGCTTGAACCTGGGAGGCAG
              |||||||||||||||||||||||||||||||||||||||||||||||||||||||| ||||||||
        58,649 CGCATGCCTATAATCCCAGCTACTCAGGAGGCTGAGGCAGGAGAATTGCTTGAACCCGGGAGGCGG  DOWNSTREAM

DELETION LOCUS: CAGGTGCCTGTAATCCCAGCTACTCAGGAGGCTGAGGCAGGAGAATTGCTTGAACCCGGGAGGCGG

FIGURE 5

```
         UPSTREAM
50,514   CATCTTCTTGGGAGGCTAAGGCAGGAGAATCGCTTGAACC-TGGAGGCAGAGGTTGCAGTGAGCCGAGATCATGCCACTGT
         ||| ||| |||||||||||||||||||||||||||||||  |||||||||||||||||||||||||||| |||   |||
76,967   CAGCTACTCAGGAGGCTAAGGCAGGAGAATCGCTTGAACCCTGGAGGCAGAGGTTGCAGTGAGCCCAGATCGCCACCACTAC   DOWNSTREAM

DELETION LOCUS:
         CATCTTCTTGGGAGGCTAAGGCAGGAGAATCGCTTGAACCTGGAGGCAGAGGTTGCAGTGAGCCCAGATCGCCACCACTAC
```

FIGURE 6

```
1505  D    D    R    W    Y    M    H    S    C    S    G    S    L    Q    N    R    1520
4513  GAT  GAT  AGG  TGG  TAC  ATG  CAC  AGT  TGC  TCT  GGG  AGT  CTT  CAG  AAT  AGA  4560
                                              EXON 15

1521  N    Y    P    S    Q    E    E    L    I    K    V    V    D    V    E    E    1536
4561  AAC  TAC  CCA  TCT  CAA  GAG  GAG  CTC  ATT  AAG  GTT  GTG  GAT  GTG  GAG  GAG  4608

1537  Q    Q    L    E    E    S    G    P    H    D    L    T    E    T    S    Y    1552
4609  CAA  CAG  CTG  GAA  GAG  TCT  GGG  CCA  CAC  GAT  TTG  ACG  GAA  ACA  TCT  TAC  4656

1553  L    P    R    Q    D    L   |----------D-|  A    E    F    V                    1696
4657  TTG  CCA  AGG  CAA  GAT  CTA G|  [Del 16-17 here]  |AT  GCT  GAG  TTT  GTG       5088

1697  C    E    R    T    L    K    Y    F    L    G    I    A    G    K    W          1712
5089  TGT  GAA  CGG  ACA  CTG  AAA  TAT  TTC  CTA  GGA  ATT  GCG  GGA  AAA  TGG        5136
                                   EXON 18

1713  V    V    S    Y    F    W    V    T    Q    S    I    K    E    R    K    M     1728
5137  GTA  GTT  AGC  TAT  TTC  TGG  GTG  ACC  CAG  TCT  ATT  AAA  GAA  AGA  AAA  ATG   5184
                                                        EXON 19
```

FIGURE 7

```
1441  D   L   R   N   P   E   Q   S   T   S   E   K   A   V   L   T   1456
4321  GAC CTG CGA AAT CCA GAA CAA AGC ACA TCA GAA AAA GCA GTA TTA ACT 4368

1457  S   Q   K   S   S   E   Y   P   I   S   Q   N   P   E   G   L   1472
4369  TCA CAG AAA AGT AGT GAA TAC CCT ATA AGC CAG AAT CCA GAA GGC CTT 4416
                                                    EXON 14
1473  S   A   D   K   F   E   V   S   A   D   S   S   T   S   K   N   1488
4417  TCT GCT GAC AAG TTT GAG GTG TCT GCA GAT AGT TCT ACC AGT AAA AAT 4464

1489  K   E   P   G   V   E  |-R(conserved)----------[Del 15 - 16 here]  C   S
4465  AAA GAA CCA GGA GTG GAA AG                                        A TGC TCG  4992

EXON 17
4993  C   T   S   G   P   E   N   T   T   S   L   STOP
      TGT ACA AGT TTG CCA GAA AAC ACC ACA TCA CTT TAA CTA ATC TAA TTA  5040

5041  CTG AAG AGA CTA CTC ATG TTG TTA TGA AAA CAG ATG CTG AGT TTG TG   5088
```

FIGURE 8

```
                EXON 12...      EXON 13...
     1393       T   T   Q   Q   R   D   T   M   Q   H   N   L   I   K   L   Q           1408
     4177       ACC ACT CAG CAG AGG GAT ACC ATG CAA CAT AAC CTG ATA AAG CTC CAG         4224

1409       Q   E   M   A   E   L   E   A   V   L   E   Q   H   G   S   Q           1424
     4225       CAG GAA ATG GCT GAA CTA GAA GCT GTG TTA GAA CAG CAT GGG AGC CAG         4272

1425       P   S   N   S   Y   P   S   I   I   S   D   S   S   A   L   E           1440
     4273       CCT TCT AAC AGC TAC CCT TCC ATC ATA AGT GAC TCT TCT GCC CTT GAG         4320

EXON 21...
     1441       D   L   R   N   P   E   Q   S   T   S   E   K  |-----\    |D   AT
     4321       GAC CTG CGA AAT CCA GAA CAA TCA ACA AGC AAA G                 
                                                    (DEL 14-20 here)

EXON 21...                 EXON 22...
                L   Q   G   A   R   N   L   L   W   A   L   H   Q   H   A
                CTT CAG GGG GCT AGA AAT CTG TTG CTA TGG GCC CTT CAC CAA CAT GCC
                                                            EXON 23...
                H   R   S   T   G   M   D   G   T   A   V   W   C   F   C   G
                CAC AGA TCA ACT GGA ATG GAT GGT ACA GCT GTG TGG TGC TTC TGT GGT
                                                                EXON 24...
                E   G   A   F   I   I   H   P   W   H   R   C   P   P   N   C
                GAA GGA GCT TTC ATC ATT CAC CCT TGG CAC AGG TGT CCA CCC AAT TGT
                G   C   A   A   R   C   L   D   R   G   Q   W   L   P   C   N
                GGT TGT GCA GCC AGA TGC CTC GAC AGA GGA CAA TGG CTT CCA TGC AAT

W   A   D   V   *
                TGG GCA GAT GTG TGA
```

FIGURE 9

LARGE DELETIONS IN HUMAN BRCA1 GENE AND USE THEREOF

CROSS-REFERENCE TO RELATED U.S. APPLICATIONS

This application claims the benefit (under 35 U.S.C. §119(e)) of U.S. Provisional Application Ser. Nos. 60/387,132 filed on Jun. 7, 2002 and 60/402,430 filed on Aug. 9, 2002, which are both incorporated herein by reference in their entirety.

TECHNICAL FIELD OF THE INVENTION

This invention generally relates to human genetics, particularly to the identification of genetic polymorphic variations in the human BRCA1 gene and methods of using the identified genetic polymorphisms.

TECHNICAL BACKGROUND OF THE INVENTION

Breast cancer susceptibility gene 1 (BRCA1) is a tumor suppressor gene identified on the basis of its genetic linkage to familial breast cancers. It is a 220-kilodalton nuclear phosphoprotein in normal cells. Mutations of the BRCA1 gene in humans are associated with predisposition to breast and ovarian cancers. In fact, BRCA1 and BRCA2 mutations are responsible for the majority of familial breast cancer. Inherited mutations in the BRCA1 and BRCA2 genes account for approximately 7-10% of all breast and ovarian cancers. Women with BRCA mutations have a lifetime risk of breast cancer between 56-87%, and a lifetime risk of ovarian cancer between 27-44%. In addition, mutations in BRCA1 gene have also been linked to various other tumors including, e.g., proliferative breast disease (PBD), papillary serous carcinoma of the peritoneum (PSCP), and prostate cancer. Schorge, et al., *J. Nat. Cancer Inst.,* 90:841-845 (1998); Arason, *Am. J. Hum. Genet.,* 52:711-717 (1993); Langston, et al., *New Eng. J. Med.,* 334: 137-142 (1996).

A large number of deleterious mutations in BRCA1 gene have been discovered. Genetic testing on patients to determine the presence or absence of such deleterious mutations has proven to be an effective approach in detecting predispositions to breast and ovarian cancers. Genetic testing is now commonly accepted as the most accurate method for diagnosing hereditary breast cancer and ovarian risk.

As deleterious mutations in BRCA1 are associated with predisposition to cancers, particularly breast cancer and ovarian cancer, it is desirable to identify additional naturally existing deleterious mutations in the BRCA1 gene, which may serve as valuable diagnostic markers. One such class of deleterious mutations includes large deletions.

SUMMARY OF THE INVENTION

The present invention is based on the discovery of a number of large deletions in human BRCA1 gene in patients. A detailed description of the newly discovered deletion mutations is provided in Table 1. These large deletions are believed to be deleterious and cause significant alterations in structure or biochemical activities in the BRCA1 gene products expressed from mutant BRCA1 genes. Patients with such deletions in one of their BRCA1 genes are predisposed to, and thus have a significantly increased likelihood of, breast cancer and/or ovarian cancer. Therefore, these deletion variants are useful in genetic testing as markers for the prediction of predisposition to cancers, especially breast cancer and ovarian cancer, and in therapeutic applications for treating cancers.

Accordingly, in a first aspect of the present invention, isolated BRCA1 nucleic acids (genomic DNAs, corresponding mRNAs and corresponding cDNAs) are provided comprising one of the newly discovered genetic variants summarized in Table I below.

In accordance with another aspect of the invention, isolated polypeptides are provided which are BRCA1 protein variants comprising at least a portion of the amino acid sequence of a BRCA1 protein. The BRCA1 protein variants are encoded by an isolated BRCA1 gene sequence of the present invention.

The present invention also provides a method for preparing an antibody to a BRCA1 protein variant according to the present invention. Preferably, the antibody prepared in this method is selectively immunoreactive with one or more of the newly discovered BRCA1 protein variants.

In accordance with another aspect of the invention, a method is provided for genotyping BRCA1 to determine whether an individual has a genetic variant or an amino acid variant identified in the present invention. The presence of the variants would indicate a predisposition to cancers including breast cancer and ovarian cancer. In accordance with this aspect of the invention, a sample containing genomic DNA, mRNA, or cDNA of the BRCA1 gene is obtained from the individual to be tested. The genomic DNA, mRNA, or cDNA of the BRCA1 gene in the sample should include at least the nucleotide sequence surrounding the locus of one or more of the above-described genetic variants such that the presence or absence of a particular genetic variant can be determined. Any suitable method known in the art for genotyping can be used for determining the nucleotide(s) at a particular position in the BRCA1 gene. Alternatively, the presence or absence of one or more of the amino acid variants disclosed in FIG. 7, 8 or 9 can also be determined in the BRCA1 protein in a sample isolated from a patient to be tested. The presence of the nucleotide and/or amino acid variants provided in the present invention may be indicative of a likelihood of a predisposition to cancers, e.g., breast cancer and ovarian cancer.

In accordance with another aspect of the present invention, a variety of methods are provided for predicting a predisposition to cancer in a patient. In one embodiment these methods comprise detecting a deletion in the BRCA1 gene that can result from an unequal crossover event between specific pairs of Alu sequences, wherein the presence of such a deletion would indicate a predisposition to cancer. The detection step used in such methods can involve the analysis of BRCA1 genomic DNA, cDNA or polypeptides. Analyses of nucleic acids in these instances can involve amplification-based approaches or hybridization-based approaches. Analyses of polypeptides can involve determining whether or not the variant BRCA1 polypeptide is truncated, or contains characteristic epitopes that can be specifically detected with an appropriate antibody.

In another embodiment of this aspect of the present invention these methods comprise detecting a deletion in the BRCA1 gene that can result from an unequal crossover event between specific repetitive sequences, commonly referred to as recombination breakpoints or regions, and presented in Table 1, wherein the presence of such a deletion would also indicate a predisposition to cancer. As with deletions resulting from the unequal crossover between specific Alu repeats, the detection step used in the methods of this embodiment can involve the analysis of BRCA1 genomic DNA, cDNA or polypeptides, and anlysis of nucleic acids can involve amplification-based approaches.

In yet another embodiment of this aspect of the present invention these methods involve detecting specific sequences in BRCA1 genomic DNA or cDNA that are formed by the joining of the normally-separated sequences that occur on either side of the deleted region. Detection of these indicative or characteristic nucleic acids in these instances can involve amplification-based approaches or hybridization-based approaches.

In accordance with another aspect of the invention, a detection kit is also provided for detecting, in an individual, an elevated risk of cancer. In a specific embodiment, the kit is used in determining a predisposition to breast cancer and ovarian cancer. The kit may include, in a partitioned carrier or confined compartment, any nucleic acid probes or primers, or antibodies useful for detecting the BRCA1 variants of the present invention as described above. The kit can also include other reagents such as reverse transcriptase, DNA polymerase, buffers, nucleotides and other items that can be used in detecting the genetic variations and/or amino acid variants according to the method of this invention. In addition, the kit preferably also contains instructions for its use.

The present invention further provides a method for identifying a compound for treating or preventing cancers associated with a BRCA1 genetic variant of the present invention. The method includes screening for a compound capable of selectively interacting with a BRCA1 protein variant of the present invention.

The foregoing and other advantages and features of the invention, and the manner in which the same are accomplished, will become more readily apparent upon consideration of the following detailed description of the invention taken in conjunction with the accompanying examples and drawings, which illustrate preferred and exemplary embodiments.

BRIEF DESCRIPTION OF THE FIGURES

FIGS. 1-6 show alignments of the upstream and downstream BRCA1 sequences involved in the unequal crossover events that resulted in deletions 1-6, respectively. Recombination likely occurred between the regions underlined in the upstream and downstream sequences, to produce the observed recombinant sequences shown (with their region of recombination underlined). These observed recombinant sequences were discovered in genomic DNA isolated from human patients. The nucleotide numbers shown correspond to the reference sequence provided by GenBank Accession Number L78833.1 (Smith et al., Genome Res. 6:1029-1049 (1996)).

FIGS. 7, 8, and 9 depict the effects or consequences of the newly discovered large deletions on the gene products of BRCA1 genes bearing such mutations. In particular, FIG. 7 illustrates the effects of newly discovered deletion Nos. 1, 2, 3, and 4, which effectively remove exons 16 and 17 from the BRCA1 gene transcript (mRNA), thereby removing the 133 codons encoding amino acid residues E1559-T1691. Although these mutations all result in a shortened mRNA transcript lacking exons 16 and 17 and a shortened mutant BRCA1 protein, they do not disrupt the open reading frame of the remaining transcript.

FIG. 8 shows the effects of newly discovered Deletion No. 5, which effectively removes exons 15 and 16 from the BRCA1 gene transcript (mRNA), thereby removing the third position nucleotide from codon R1495 and the following 167 codons encoding amino acid residues S1496-F1661. Removal of the third position nucleotide of codon R1495 serves to disrupt the downstream open reading frame, resulting in a frame shift that is maintained until an ochre stop codon is encountered fourteen codons into exon 17. As a result of the frame-shift created by the removal of exons 15 and 16 from the spliced gene transcript, a novel 13-amino acid sequence encoded by the frame-shifted exon 17 (SEQ ID NO:13) is append onto R1495 of the translated BRCA1 polypeptide, and the overall length of the resulting BRCA1 protein is shortened from 1863 to 1507 amino acid residues.

FIG. 9 depicts the effects of newly discovered deletion No. 6, which effectively removes exons 14 through 20 from the BRCA1 gene transcript (mRNA), thereby removing the second and third position nucleotides from codon A1452 and the following 306 codons encoding amino acid residues V1453-K1758. Removal of second and third position nucleotides from codon A1453 serves to disrupt the downstream open reading frame, resulting in a translational frame shift that is maintained through the codons encoded by exons 21, 22, 23 and 24, until a UGA stop codon is encountered 7 codons into exon 24. As a result of the frame-shift created by the removal of exons 14 through 20 from the spliced gene transcript, a novel 69-amino acid sequence encoded by the frame-shifted exons 21, 22, 23, and 24 (SEQ ID NO:14) is append onto K1452 of the translated BRCA1 polypeptide, and the overall length of the resulting BRCA1 protein is shortened from 1863 to 1521 amino acid residues.

Note: For FIGS. 1-6, the BRCA1 genomic DNA nucleotide or basepair numbers correspond to the reference sequence provided by GenBank Accession Number L78833.1. For FIGS. 7, 8, and 9, the BRCA1 cDNA nucleotide and amino acid numbers correspond to the reference sequence provided by GenBank Accession No. U14680.1.

DETAILED DESCRIPTION OF THE INVENTION

1. Definitions

The terms "genetic variant," "mutation," and "nucleotide variant" are used herein interchangeably to refer to changes or alterations to a reference BRCA1 gene sequence at a particular locus, including, but not limited to, nucleotide base deletions, insertions, inversions, and substitutions in the coding and noncoding regions. Deletions may be of a single nucleotide, a portion or a region of the nucleotide sequence of the gene, or of the entire gene sequence. Insertions may be of one or more nucleotides. The genetic variants may occur in transcriptional regulatory regions, untranslated regions of mRNA, exons, introns, or exon/intron junctions. The genetic variants may or may not result in stop codons, frame shifts, deletion of amino acids, altered amino acid sequence, or altered protein expression level. The mutations or genetic variants can be somatic, i.e., occur only in certain tissues of the body and are not inherited in the germline, or germline mutations, i.e., inherited mutations found in all tissues.

"Genetic polymorphism" as used herein refers to the phenomena that two or more genetic variants in a particular locus of a gene are found in a population.

The term "allele" or "gene allele" is used herein to refer generally to a naturally occurring gene having the reference sequence or a gene containing a specific genetic variant.

As used herein, the term "BRCA1 nucleic acid" means a nucleic acid molecule the nucleotide sequence of which is found uniquely in a BRCA1 gene or a substantially equivalent form thereof. That is, the nucleotide sequence of a "BRCA1 nucleic acid" can be a full-length sequence of, or a portion found in, either BRCA1 genomic DNA or mRNA/cDNA, either wild-type or naturally existing variant BRCA1 gene, or an artificial nucleotide sequence encoding a wild-type BRCA1 protein or naturally existing polymorphic variant BRCA1 protein.

The term "BRCA1 nucleic acid variant" refers to a naturally existing BRCA1 nucleic acid.

As used herein, the term "amino acid variant" refers to amino acid changes to a reference BRCA1 protein sequence resulting from nucleotide variants or mutations to the reference gene encoding the reference BRCA1 protein. The term "amino acid variant" is intended to encompass not only single amino acid substitutions, but also amino acid deletions, insertions, and other significant changes of amino acid sequence in a BRCA1 protein.

The term "BRCA1 protein variant" is used herein relative to a reference BRCA1 protein to mean a BRCA1 protein found in a population that is the coding product of a BRCA1 gene allele containing genetic variants such as single nucleotide substitutions, insertions, deletions, and DNA rearrangements, which lead to alterations in the protein sequence of the protein variant.

The term "locus" refers to a specific position or site in a nucleotide sequence of a gene, or amino acid sequence of a protein. Thus, there may be one or more contiguous nucleotides in a particular gene locus, or one or more amino acids at a particular locus in a polypeptide. Moreover, "locus" may also be used to refer to a particular position in a gene sequence where one or more nucleotides have been deleted, inserted, or inverted.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms.

Examples of modified forms include, but are not limited to, glycosylated forms, phosphorylated forms, myristoylated forms, palmitoylated forms, ribosylated forms, acetylated forms, etc. Modifications also include intra-molecular crosslinking and covalent attachment of various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

The terms "primer," "probe," and "oligonucleotide" may be used herein interchangeably to refer to a relatively short nucleic acid fragment or sequence. They can be DNA, RNA, or a hybrid thereof, or chemically modified analogs or derivatives thereof. Typically, they are single-stranded. However, they can also be double-stranded having two complementing strands that can be separated apart by denaturation. Normally, they have a length of from about 8 nucleotides to about 200 nucleotides, preferably from about 12 nucleotides to about 100 nucleotides, and more preferably about 18 to about 50 nucleotides. They can be labeled with detectable markers or modified in any conventional manners for various molecular biological applications.

The term "isolated," when used in reference to nucleic acids (which include gene sequences or fragments) of this invention, is intended to mean that a nucleic acid molecule is present in a form other than found in nature in its original environment with respect to its association with other molecules. For example, since a naturally existing chromosome includes a long nucleic acid sequence, an "isolated nucleic acid" as used herein means a nucleic acid molecule having only a portion of the nucleic acid sequence in the chromosome but not one or more other portions present on the same chromosome. Thus, for example, an isolated gene typically includes no more than 25 kb of naturally occurring nucleic acid sequence which immediately flanks the gene in the naturally existing chromosome or genomic DNA. However, it is noted that an "isolated nucleic acid" as used herein is distinct from a clone in a conventional library such as genomic DNA library and cDNA library in that the clones in a library are still in admixture with almost all the other nucleic acids in a chromosome or a cell. An isolated nucleic acid can be in a vector.

The term "isolated nucleic acid" embraces "purified nucleic acid" which means a specified nucleic acid is in a substantially homogenous preparation of nucleic acid substantially free of other cellular components, other nucleic acids, viral materials, or culture medium, or chemical precursors or by-products associated with chemical reactions for chemical synthesis of nucleic acids. Typically, a "purified nucleic acid" can be obtained by standard nucleic acid purification methods. In a purified nucleic acid, preferably the specified nucleic acid molecule constitutes at least 15 percent of the total nucleic acids in the preparation. The term "purified nucleic acid" also means nucleic acids prepared from a recombinant host cell (in which the nucleic acids have been recombinantly amplified and/or expressed), or chemically synthesized nucleic acids.

The term "isolated nucleic acid" also encompasses a "recombinant nucleic acid" which is used herein to mean a hybrid nucleic acid produced by recombinant DNA technology having the specified nucleic acid molecule covalently linked to one or more nucleic acid molecules that are not the nucleic acids naturally flanking the specified nucleic acid. Typically, such nucleic acid molecules flanking the specified nucleic acid are no more than 50 kb. In addition, the specified nucleic acid may have a nucleotide sequence that is identical to a naturally occurring nucleic acid, or a modified form, or mutant form thereof having one or more mutations such as nucleotide substitution, deletion/insertion, inversion, and the like.

In addition, "isolated nucleic acid" further includes a chemically synthesized nucleic acid having a naturally occurring nucleotide sequence or an artificially modified form thereof (e.g., dideoxy forms).

The term "isolated polypeptide" as used herein means a polypeptide molecule is present in a form other than found in nature in its original environment with respect to its association with other molecules. The term "isolated polypeptide" encompasses a "purified polypeptide" which is used herein to mean that a specified polypeptide is in a substantially homogenous preparation, substantially free of other cellular components, other polypeptides, viral materials, or culture medium, or when the polypeptide is chemically synthesized, substantially free of chemical precursors or by-products associated with the chemical synthesis. For a purified polypeptide, preferably the specified polypeptide molecule constitutes at least 15 percent of the total polypeptide in the preparation. A "purified polypeptide" can be obtained from natural or recombinant host cells by standard purification techniques, or by chemical synthesis.

The term "isolated polypeptide" also encompasses a "recombinant polypeptide," which is used herein to mean a hybrid polypeptide produced by recombinant DNA technology or chemical synthesis having a specified polypeptide molecule covalently linked to one or more polypeptide molecules which do not naturally link to the specified polypeptide.

As used herein, "haplotype" is a combination of genetic (nucleotide) variants in a region of an mRNA or a genomic DNA on a chromosome found in an individual. Thus, a haplotype includes a number of genetically linked polymorphic variants that are typically inherited together as a unit.

The term "reference sequence" refers to a polynucleotide or polypeptide sequence known in the art, including those disclosed in publicly accessible databases (e.g., GenBank), or a newly identified gene sequence, used simply as a reference with respect to the variants provided in the present invention. The nucleotide or amino acid sequence in a reference sequence is contrasted to the alleles disclosed in the present invention having newly discovered nucleotide or amino acid variants.

The terms "crossing-over" and "crossover," are used interchangeably herein, to refer to the reciprocal exchange of material between chromosome homologs—by breakage and reunion—that occurs during meiosis and is responsible for genetic recombination. The term "unequal crossover," as used herein, refers to a crossover event occurring between homologous sequences in paired chromosome homologs that are not perfectly aligned, or, more generally, describes a recombination event in which the two recombining sites lie at nonidentical locations in the two parental DNA molecules. The products of an unequal crossover are two chromosomes, or more generally two progeny DNA molecules, one of which bears a deletion, and the other of which bears a duplication of the nucleotide sequence residing between the mispaired homologous sequences or recombining sites.

2. Nucleotide and Amino Acid Variants

Smith and coworkers described the complete genomic sequence of a 117 kilobase region of human DNA containing the BRCA1 gene, and deposited the nucleotide sequence of the genomic DNA in the GenBank under the Accession Number L78833.1 (Smith et al., *Genome Res.*, 6:1029–1049 (1996)). This nucleotide sequence (referred to as L78833.1) is used herein as a reference sequence for identifying the polymorphic positions of the large deletions of the present invention and the upstream and downstream sequences that were likely involved in the unequal crossover events that yielded Deletion Nos. 1-6. The complete coding sequence corresponding to the mRNA transcribed from the BRCA1 gene, and the amino acid sequence encoded therein, were deposited in the GenBank under Accession Number U14680.1. These sequences (cDNA and amino acid) are used as reference sequences for identifying the effects or consequences of the large deletions at the level of the gene transcript (mRNA), cDNA and encoded protein.

In accordance with the present invention, analysis of the nucleotide sequence of genomic DNA corresponding to the BRCA1 genes of specific human patients has led to the discovery of a number of mutant BRCA1 alleles that exhibit large deletions relative to the reference sequence provided by GenBank Accession No. L78833.1. Specifically, six different genetic variants exhibiting large deletions have been discovered. These six different genetic variants, and the effects or consequences they have on the gene products expressed from the BRCA1 alleles that bear them, are summarized in Table 1. Of these six different genetic variants corresponding to six different large deletions of nucleotide sequence within the BRCA1 gene, four result in the deletion of exons 16 and 17, one results in deletion of exons 15 and 16, and one results in deletion of exons 14 through 20, in the mRNAs transcribed from the variant alleles.

TABLE I

GENETIC VARIANTS OF THE BRCA1 GENE
All numeric designation of nucleotides conform to the sequence in Smith et al.,
Genome Res., 6:1029–1049 (1996) and GenBank Accession Number L78833.1

| Deletion No. | Recombination Breakpoint | | Size of Deletion (bp) | Exons Removed | Consequences of Deletion |
|---|---|---|---|---|---|
| | 5' Region (nt positions) | 3' Region (nt positions) | | | |
| 1 | 56,960–56,998 | 63,296–63,334 | 6,337 | 16 & 17 | Removal of residues E1559-T1691 |
| 2 | 54,960–54,965 | 62,143–62,147 | 7,183 | 16 & 17 | Removal of residues E1559-T1691 |
| 3 | 55,893–55,932 | 62,049–62,088 | 6,157 | 16 & 17 | Removal of residues E1559-T1691 |
| 4 | 56,090–56,095 | 61,838–61,843 | 5,749 | 16 & 17 | Removal of residues E1559-T1691 |
| 5 | 53,030–53,075 | 58,659–58,704 | 5,629 | 15 & 16 | Addition of a novel 13-residue carboxyl-terminus onto R1495 |
| 6 | 50,524–50,577 | 76,977–77,031 | 26,454 | 14–20 | Addition of a novel 69-residue carboxyl-terminus onto K1452 |

In further accordance with the present invention, the large deletions described in Table 1 were found in patients at high risk of developing breast cancer. Nucleotide sequences obtained from these individuals indicate that all six of these large deletions involved the joining of a particular sequence in a more 5' region of the BRCA1 gene (an upstream sequence), to a similar sequence in a more 3' region of the BRCA1 gene (a downstream sequence) to create a recombined or joined sequence that spans the deletion locus. Further analysis has shown that all upstream sequences, and all downstream sequences reside within identified Alu repeats (Smith et al, *Genome Res.*, 6:1029-1049 (1996)). Consequently, the observed mutations most likely arose from an unequal crossover event occurring between misaligned Alu sequences in the BRCA1 genes of paired homologous chromosomes. The specific sequences of the upstream and downstream loci involved in these six unequal crossover events, along with the specific joined or recombined sequences resulting from these unequal crossover events (the "deletion loci"), which have been observed in the genomic DNA of specific individuals, are shown in FIGS. 1-6. The consequences of each of the large deletions observed in mutant BRCA1 genomic DNAs (as depicted in FIGS. 1-6) on the nucleotide sequence of the mRNA transcript transcribed therefrom (or on the corresponding cDNA), as well as on the amino acid sequence of the encoded protein, are shown in FIGS. 7-9.

The breakpoint regions (upstream and downstream loci) believed to be responsible for the unequal crossover that resulted in Deletion No. 1, and the resulting recombined nucleotide sequence discovered in human patients are shown underlined in FIG. 1. As indicated in Table 1, the 5' recombination breakpoint resides between nucleotides 56,960 and 56,998 (underlined in the upstream sequence) and the 3' recombination breakpoint resides between nucleotides 63,296 and 63,334 (underlined in the downstream sequence). Recombination between the upstream and downstream breakpoint regions has resulted in the deletion of 6,337 basepairs of the BRCA1 gene and has produced a novel BRCA1 gene sequence comprising the junction sequence provided by SEQ ID NO:1. The resulting recombined genomic DNA sequence, which when transcribed directs the expression of mutant mRNAs lacking exons 16 and 17 (FIG. 7), was found in three individuals.

The loci (breakpoint regions) believed to be responsible for the unequal crossover that resulted in Deletion No. 2, and the resulting recombined nucleotide sequence discovered in human patients are shown underlined in FIG. 2. As indicated in Table 1, the 5' recombination breakpoint resides between nucleotides 54,960 and 54,965 (underlined in the upstream sequence) and the 3' recombination breakpoint resides between nucleotides 62,143 and 62,147 (underlined in the downstream sequence). Recombination between the upstream and downstream breakpoint regions has resulted in the deletion of 7,183 basepairs of the BRCA1 gene and has produced a novel BRCA1 gene sequence comprising the junction sequence provided by SEQ ID NO:2. The resulting recombined genomic DNA sequence, which when transcribed also directs the expression of mutant mRNAs lacking exons 16 and 17 (FIG. 7), was identified in one individual.

The loci (breakpoint regions) believed to be responsible for the unequal crossover that resulted in Deletion No. 3, and the resulting recombined nucleotide sequence discovered in human patients are shown underlined in FIG. 3. As indicated in Table 1, the 5' recombination breakpoint resides between nucleotides 55,893 and 55,932 (underlined in the upstream sequence) and the 3' recombination breakpoint resides between nucleotides 62,048 and 62,087 (underlined in the downstream sequence). Recombination between the upstream and downstream breakpoint regions has resulted in the deletion of 6,157 basepairs of the BRCA1 gene and has produced a novel BRCA1 gene sequence comprising the junction sequence provided by SEQ ID NO:3. The resulting recombined genomic DNA sequence, which when transcribed also directs the expression of mutant mRNAs lacking exons 16 and 17 (FIG. 7), was characterized in one individual.

The loci (breakpoint regions) believed to be responsible for the unequal crossover that resulted in Deletion No. 4, and the resulting recombined nucleotide sequence discovered in human patients are shown underlined in FIG. 4. As indicated in Table 1, the 5' recombination breakpoint resides between nucleotides 56,090 and 56,095 (underlined in the upstream sequence) and the 3' recombination breakpoint resides between nucleotides 61,838 and 61,843 (underlined in the downstream sequence). Recombination between the upstream and downstream breakpoint regions has resulted in the deletion of 5,749 basepairs of the BRCA1 gene and has produced a novel BRCA1 gene sequence comprising the junction sequence provided by SEQ ID NO:4. The resulting recombined genomic DNA sequence, which when transcribed also directs the expression of mutant mRNAs lacking exons 16 and 17 (FIG. 7), was found in one individual.

The loci (breakpoint regions) believed to be responsible for the unequal crossover that resulted in Deletion No. 5, and the resulting recombined nucleotide sequence discovered in human patients are shown underlined in FIG. 5. As indicated in Table 1, the 5' recombination breakpoint resides between nucleotides 53,030 and 53,075 (underlined in the upstream sequence) and the 3' recombination breakpoint resides between nucleotides 58,659 and 58,704 (underlined in the downstream sequence). Recombination between the upstream and downstream breakpoint regions has resulted in the deletion of 5,629 basepairs of the BRCA1 gene and has produced a novel BRCA1 gene sequence comprising the junction sequence provided by SEQ ID NO:5. The resulting recombined genomic DNA sequence, which when transcribed also directs the expression of mutant mRNAs lacking exons 15 and 16 (FIG. 8), was identified in one individual.

The loci (breakpoint regions) believed to be responsible for the unequal crossover that resulted in Deletion No. 6, and the resulting recombined nucleotide sequence discovered in human patients are shown underlined in FIG. 6. As indicated in Table 1, the 5' recombination breakpoint resides between nucleotides 50,524 and 50,577 (underlined in the upstream sequence) and the 3' recombination breakpoint resides between nucleotides 76,977 and 77,031 (underlined in the downstream sequence). Recombination between the upstream and downstream breakpoint regions has resulted in the deletion of 26,454 basepairs of the BRCA1 gene and has produced a novel BRCA1 gene sequence comprising the junction sequence provided by SEQ ID NO:6. The resulting recombined genomic DNA sequence, which when transcribed also directs the expression of mutant mRNAs lacking exons 14 through 20 (FIG. 9), has now been characterized in fourteen individuals.

The consequences of Deletions 1-6 on the gene products encoded by the BRCA1 alleles bearing these mutations are depicted in FIGS. 7-9. As mentioned above, Deletion Nos. 1, 2, 3, and 4 all produce mutant alleles of the BRCA1 gene that, when transcribed, direct the expression of mRNAs lacking exons 16 and 17 (FIG. 7). Such mRNAs, and cDNAs prepared from them, lack the codons encoding amino acid residues E1559-T1691, and are characterized by the novel junction sequence comprising SEQ ID NO:7, which spans the deleted codons. Despite the omission of the 133 codons encoded by exons 16 and 17, the open reading frame of the remaining nucleotides is not disrupted (i.e., ntG4675 carries over to ntA5075 and ntT5076, so that aaD1692 is conserved). Consequently, the mRNAs transcribed from the mutant alleles characterized by Deletion Nos. 1-4, direct the translation of a mutant BRCA1 protein comprised of 1,730 amino acid residues, instead of the normal 1,863. These shorter mutant BRCA1 proteins are characterized by the amino acid sequence created by the juxtaposition of the codon encoding L1558 with the codon encoding D1692, and comprising SEQ ID NO:10.

In contrast, Deletion No. 5 produces a mutant allele of the BRCA1 gene that, when transcribed, directs the expression of mRNA lacking exons 15 and 16 (FIG. 8). Such mRNA, and the cDNA prepared from it, lacks the codons encoding amino acid residues S1496-F1662, as well as the third position nucleotide from codon R1495, and is characterized by the novel junction sequence comprising SEQ ID NO:8, which spans the region of the deleted codons. Unlike with Deletions Nos. 1-4, mRNA transcribed from mutant BRCA1 alleles encompassing Deletion No. 5 directs a translational frame shift downstream of the junction between nucleotides encoded by exons 14 and 17. Translation in the shifted frame is maintained until an ochre stop codon is encountered fourteen codons into exon 17. As a result of the frame-shift created by the omission of exons 15 and 16, a novel 13-amino acid sequence (SEQ ID NO:13), encoded by codons within the frame-shifted exon 17, is appended onto R1495 of the translated mutant BRCA1 polypeptide, and the overall length of the BRCA1 protein is shortened from 1863 to 1507 amino acid residues. Consequently, these mutant BRCA1 proteins are characterized by their shortened length, their novel carboxy-termini, and by the unique amino acid sequence created by the splicing of exons 14 and 17, which comprises SEQ ID NO:11.

Deletion No. 6 produces a mutant allele of the BRCA1 gene that, when transcribed, directs the expression of mRNA lacking exons 14 through 20 (FIG. 9). Such mRNA, and the cDNA prepared from it, lacks the codons encoding amino acid residues V1453-K1758, as well as the second and third position nucleotides from codon A1453, and is characterized by the novel junction sequence comprising SEQ ID NO:9, which spans the deleted codons. Like Deletion No. 5, Deletion No. 6 directs a translational frame shift downstream of the junction between nucleotides encoded by exons 13 and 21. Translation in the shifted frame is maintained through the codons encoded by exons 21, 22, 23 and 24, until a UGA stop is encountered 7 codons into exon 24. As a result of the frame-shift created by the omission of exons 14 through 20, a novel 69-amino acid sequence (SEQ ID NO:14) is appended onto K1452 of the translated mutant BRCA1 polypeptide, and the overall length of the BRCA1 protein is shortened from 1863 to 1521 amino acid residues. Consequently, these mutant BRCA1 proteins are also characterized by their shortened length, their novel carboxy-termini, and by the unique amino acid sequence created by the splicing of exons 13 and 21, which comprises SEQ ID NO:12.

As shown in the Figures, and described above, the genetic variants according to the present invention are expected to cause significant changes in the structure and biological activity of the BRCA1 protein they encode. Individuals who inherit such genetic variants (large deletion mutations) are predisposed to cancers, particularly breast cancer and ovarian cancer.

3. BRCA1 Nucleic Acids

In a first aspect of the present invention, isolated nucleic acids are provided comprising a nucleotide sequence of a BRCA1 nucleic acid variant identified in accordance with the present invention. The nucleotide sequence is at least 12, 13, 14, 15, 17, 18, 19, 20, 25, 30, or 35 contiguous nucleotides spanning the deletion locus in one of the mutant BRCA1 genomic DNAs having one of the Deletion Nos. 1-6, or the deletion locus in one of the mutant BRCA1 mRNAs, or cDNAs prepared therefrom, expressed from the mutant BRCA1 genomic DNAs having one of the Deletion Nos. 1-6. The nucleic acid molecules can be in a form of DNA, RNA, or a chimeric or hybrid thereof, and can be in any physical structures including a single-strand or double-strand or in the form of a triple helix.

In one embodiment, the isolated nucleic acids have a sequence selected from the group consisting of SEQ ID NOs:1-9 or 15-82, and complements thereof. Specifically, SEQ ID NOs:1 and 15-17 are mutant sequences seen in the BRCA1 genomic DNA variant that resulted from Deletion No. 1. SEQ ID NOs:2 and 18-23 are mutant sequences seen in the BRCA1 genomic DNA variant that resulted from Deletion No. 2. SEQ ID NOs:3 and 24-27 are mutant sequences seen in the BRCA1 genomic DNA variant that resulted from Deletion No. 3. SEQ ID NOs:4 and 28-32 are mutant sequences seen in the BRCA1 genomic DNA variant that resulted from Deletion No. 4. SEQ ID NOs:5 and 33-36 are mutant BRCA1 genomic sequences that resulted from Deletion No. 5. And, SEQ ID NOs:6 and 37-41 are mutant BRCA1 genomic sequences that resulted from Deletion No. 6.

In addition, SEQ ID NOs:7 and 42-52 are mutant BRCA1 cDNA sequences that span the cDNA deletion locus that results from Deletion Nos. 1, 2, 3, and 4. SEQ ID NOs:45-47 are portions of the antisense strand sequence of the mutant BRCA1 cDNA resulted from Deletion Nos. 1, 2, 3, and 4, while SEQ ID NOs:7, 42-44, and 48-52 are portions of the sense strand that also span the cDNA deletion locus resulted from Deletion Nos. 1, 2, 3, and 4.

SEQ ID NOs:8, 53-57, and 64-66 are portions of the sense strand of mutant BRCA1 cDNA sequences that span the cDNA deletion locus resulted from Deletion No. 5, while SEQ ID NOs:58-63 are portions of the antisense strand sequence of the mutant BRCA1 cDNA resulted from Deletion No. 5.

SEQ ID NOs:9, 67-74, and 64-66 are portions of the sense strand of mutant BRCA1 cDNA sequences that span the cDNA deletion locus resulted from Deletion No. 6, while SEQ ID NOs:75-79 are portions of the antisense strand sequence of the mutant BRCA1 cDNA resulted from Deletion No. 6.

SEQ ID NOs:80 represents the portion of the cDNA encoding the novel carboxyl-terminal tail of the mutant BRCA1 polypeptide resulting from Deletion No. 5. SEQ ID NO:81 represents the cDNA encompassing the junction of the original reading frame and the novel frame-shifted reading frame that results from the juxtaposition of exons 13 and 21 seen in the mutant BRCA1 mRNA resulting from Deletion No. 6, while SEQ ID NO:82 represents the portion of the cDNA encoding the novel carboxyl-terminal tail of the mutant BRCA1 polypeptide resulting from Deletion No. 6.

In a specific embodiment, the isolated nucleic acids of the present invention are isolated BRCA1 nucleic acid having a sequence according to one of SEQ ID NOs:1-9 or 15-82, or complements thereof. Preferably, the isolated BRCA1 nucleic acids are isolated BRCA1 nucleic acid variants that are mutant BRCA1 genomic DNAs having one of the Deletion Nos. 1-6, or those mutant BRCA1 mRNAs derived from the mutant BRCA1 genomic DNAs, having one of the Deletion Nos. 1-6, or cDNAs derived from such mRNAs. The BRCA1 genomic DNAs, cDNAs and mRNAs can have a full-length sequence (i.e., including the entire coding regions and, in the case of genomic DNAs, optionally introns, promoter, and other regulatory sequences) or partial sequence (i.e., a portion of the full-length sequence).

In one embodiment, an isolated BRCA1 nucleic acid is an oligonucleotide, primer or probe comprising a contiguous span of the nucleotide sequence of a mutant BRCA1 sequence (either genomic DNA or cDNA or mRNA sequence) provided in accordance with the present invention and spanning a cDNA deletion locus resulted from Deletion Nos. 1, 2, 3, 4, 5 or 6. The oligonucleotide, primer or probe contains at least 12, preferably from about 15, 18, 20, 22, 25, 30, 40 to about 50, 60, 70, 80, 90, or 100, and more preferably from about 30 to about 50 nucleotides. In one embodiment, the oligonucleotides, primers and probes are specific to a BRCA1 nucleic acid variant of the present invention. That is, they selectively hybridize, under stringent conditions generally recognized in the art, to a BRCA1 nucleic acid variant of the present invention, but do not substantially hybridize to a reference BRCA1 nucleic acid sequence under stringent conditions. Such oligonucleotides will be useful in hybridization-based methods, or alternatively amplification-based methods, for detecting the nucleotide variants of the present invention as described in detail below. A skilled artisan would recognize various stringent conditions that enable the oligonucleotides of the present invention to differentiate between a reference BRCA1 gene sequence and an isolated BRCA1 nucleic acid variant of the present invention. For example, the hybridization can be conducted overnight in a solution containing 50% formamide, 5×SSC, pH7.6, 5× Denhardt's solution, 10% dextran sulfate, and 20 microgram/ml denatured, sheared salmon sperm DNA. The hybridization filters can be washed in 0.1×SSC at about 65° C.

The oligonucleotide primers or probes of the present invention can have a detectable marker selected from, e.g., radioisotopes, fluorescent compounds, enzymes, or enzyme co-factors operably linked to the oligonucleotide. The primers, probes and oligonucleotide sequences of the present invention are useful in genotyping and haplotyping as will be apparent from the description below.

In another specific embodiment, BRCA1 nucleic acids are provided having 100, 200, 300, 400 or 500 nucleotides or basepairs, which contain the BRCA1 variant nucleotide or basepair sequences provided by SEQ ID NOs:1-9 or 15-82, and/or the complements thereof. Such nucleic acids can be DNA or RNA, and single-stranded or double-stranded.

It should be understood that any nucleic acid molecules containing a sequence according to one of SEQ ID NOs: 1-9 or 15-82 fall within the scope of this invention. For example, a hybrid nucleic acid molecule may be provided having a sequence according to one of SEQ ID NOs: 1-9 or 15-82 operably linked to a non-BRCA1 sequence such that the hybrid nucleic acid encodes a hybrid protein having a mutant BRCA1 peptide sequence. In another embodiment, the present invention provides a vector construct containing one of the nucleic acid molecules of the present invention. As will be apparent to skilled artisans, the vector may be employed to amplify a nucleic acid molecule of the present invention that is contained in the vector construct. Alternatively, the vector construct may be used in expressing a polypeptide encoded by a nucleic acid molecule of the present invention that is contained in the vector construct. Generally, the vector construct may include a promoter operably linked to an isolated nucleic acid molecule (including a full-length sequence or a fragment thereof in the 5' to 3' direction or in the reverse direction for the purpose of producing antisense nucleic acids), an origin of DNA replication for the replication of the vectors in host cells and a replication origin for the amplification of the vectors in, e.g., *E. coli*, and selection marker(s) for selecting and maintaining only those host cells harboring the vectors. Additionally, the vectors preferably also contain inducible elements, which function to control the expression of the isolated gene sequence. Other regulatory sequences such as transcriptional termination sequences and translation regulation sequences (e.g., Shine-Dalgarno sequence) can also be included. An epitope tag coding sequence for detection and/or purification of the encoded polypeptide can also be incorporated into the vector construct. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. The vector construct can be introduced into the host cells or organisms by any techniques known in the art, e.g., by direct DNA transformation, microinjection, electroporation, viral infection, lipofection, biolystics (gene gun), and the like. The vector construct can be maintained in host cells in an extrachromosomal state, i.e., as self-replicating plasmids or viruses. Alternatively, the vector construct can be integrated into chromosomes of the host cells by conventional techniques such as selection of stable cell lines or site-specific recombination. The vector construct can be designed to be suitable for expression in various host cells, including but not limited to bacteria, yeast cells, plant cells, insect cells, and mammalian and human cells. A skilled artisan will recognize that the designs of the vectors can vary with the host used.

In another embodiment, a BRCA1 nucleic acid of the present invention is incorporated in a microchip or microarray, or other similar structures. The microarray will allow rapid genotyping and/or haplotyping in a large scale. As is known in the art, in microchips, a large number of different nucleic acids are attached or immobilized in an array on a solid support, e.g., a silicon chip or glass slide. Target nucleic acid sequences to be analyzed can be contacted with the immobilized nucleic acids on the microchip. See Lipshutz et al., *Biotechniques*, 19:442-447 (1995); Chee et al., *Science*, 274:610-614 (1996); Kozal et al., *Nat. Med.* 2:753-759 (1996); Hacia et al., *Nat. Genet.*, 14:441-447 (1996); Saiki et al., *Proc. Natl. Acad. Sci. USA*, 86:6230-6234 (1989); Gingeras et al., *Genome Res.*, 8:435-448 (1998). The microchip technologies combined with computerized analysis tools allow large-scale high throughput screening. See, e.g., U.S. Pat. No. 5,925,525 to Fodor et al; Wilgenbus et al., *J. Mol. Med.*, 77:761-786 (1999); Graber et al., *Curr. Opin. Biotechnol.*, 9:14-18 (1998); Hacia et al., *Nat. Genet.*, 14:441-447 (1996); Shoemaker et al., *Nat. Genet.*, 14:450-456 (1996); DeRisi et al., *Nat. Genet.*, 14:457-460 (1996); Chee et al., *Nat. Genet.*, 14:610-614 (1996); Lockhart et al., *Nat. Genet.*, 14:675-680 (1996); Drobyshev et al., *Gene*, 188:45-52 (1997).

In a preferred embodiment, a microarray is provided comprising a plurality of the nucleic acids of the present invention such that the nucleotide identity at each of the genetic variant sites disclosed in Table I can be determined in one single microarray.

4. BRCA1 Polypeptides

The present invention also provides isolated polypeptides having a novel amino acid sequence of a BRCA1 protein variant identified in accordance with the present invention. The amino acid sequence is a contiguous sequence of at least 3, 4, 5, 6, 7, 8, 9, 10, 12, or 13 amino acids spanning the deletion locus resulted from Deletion Nos. 1, 2, 3, 4, 5, or 6. In addition, the amino acid sequence can also be a contiguous sequence of at least 3, 4, 5, 6, 7, 8, 9, 10, 12, or 13 amino acids within the carboxyl-terminal sequence of 13 amino acids of the BRCA1 protein variant resulting from Deletion No. 5. Alternatively, the amino acid sequence can be a contiguous sequence of at least 5, 6, 7, 8, 9, 10, 12, 14, 16, 18, 20, 25, 30, 35, 40 45, 50, 55, 60, 65, or 69 amino acids within the carboxyl-terminal sequence of 69 amino acids of the BRCA1 protein variant resulting from Deletion No. 6.

In one embodiment, the isolated polypeptides of the present invention comprise an amino acid sequence according to one of SEQ ID NOs:10-14 or 83-93. The isolated polypeptide of the present invention can have at least 7, 8, 9, or more amino acids in length, preferably 10 or more, more preferably 25 or more, and even more preferably 50 or more amino acids.

The isolated polypeptides of the present invention comprising an amino acid sequence according to one of SEQ ID NOs:10 and 83-87 represent novel amino acid sequence fragments of the BRCA1 protein variant resulting from Deletion Nos. 1, 2, 3 or 4. As illustrated in FIG. 7, and described above, these polypeptides correspond to codon sequences in mutant mRNAs created by the direct splicing of exon 15 to exon 18—mutant mRNAs that are transcribed from mutant alleles of the BRCA1 gene bearing either Deletion No. 1, 2, 3, or 4—and all contain certain amino acid residues encoded by codons representing both exons. Hence, the isolated polypeptides of the present invention comprising an amino acid sequence according to one of SEQ ID NOs:10-14 or 83-93 all represent novel junction polypeptides in which amino acid residues encoded by exon 15 are joined with amino acid residues encoded by exon 18.

Similarly, the isolated polypeptides of the present invention comprising an amino acid sequence according to one of SEQ ID NOs:11, 88, and 89 represent novel amino acid sequence fragments of the BRCA1 protein variant resulting from Deletion No. 5. As shown in FIG. 8, and described above, these polypeptides correspond to codon sequences in mutant mRNAs created by the direct splicing of exon 14 to exon 17—mutant mRNAs that are transcribed from mutant alleles of the BRCA1 gene bearing Deletion No. 5—and all contain certain amino acid residues encoded by codons representing both exons. Hence, the isolated polypeptides of the present invention comprising an amino acid sequence according to one of SEQ ID NOs:11, 88, and 89 all represent novel junction polypeptides in which amino acid residues encoded by exon 14 are joined with amino acid residues encoded by exon 17.

And, the isolated polypeptides of the present invention comprising an amino acid sequence according to one of SEQ ID NOs:12 and 91-93 represent novel amino acid sequence fragments of the BRCA1 protein variant resulting from Deletion No. 6. As depicted in FIG. 9, and described above, these polypeptides correspond to codon sequences in mutant mRNAs created by the direct splicing of exon 13 to exon 21—mutant mRNAs that are transcribed from mutant alleles of the BRCA1 gene bearing Deletion No. 6—and all contain certain amino acid residues encoded by codons representing both exons. Hence, the isolated polypeptides of the present invention comprising an amino acid sequence according to one of SEQ ID NOs:12 and 91-93 all represent novel junction polypeptides in which amino acid residues encoded by exon 13 are joined with amino acid residues encoded by exon 21.

Further, the isolated polypeptides of the present invention comprising an amino acid sequence according to one of SEQ ID NOs:13 and 90 represent novel amino acid sequence fragments of a new carboxy-terminus added to the BRCA1 protein variant resulting from Deletion No. 5. As illustrated in FIG. 8, these polypeptides are encoded by codons in exon 17 which are translated from a shifted reading frame created by the the splicing of exon 14 to exon 17.

Similarly, the isolated polypeptide of the present invention comprising an amino acid sequence according to SEQ ID NO:14 represent a novel amino acid sequence fragments of a new carboxy-terminus added to the BRCA1 protein variant resulting from Deletion No. 6. As illustrated in FIG. 9, this polypeptide is encoded by codons in exons 21, 22, 23 and 24 which are translated from a shifted reading frame created by the the splicing of exon 13 to exon 21.

In a specific embodiment, the present invention provides isolated BRCA1 protein variants having one or more amino acid sequences according to one of SEQ ID NOs:10-14 or 83-93. For example, the isolated BRCA1 protein variant can be the protein variant isolated from a patient having Deletion No. 1, 2, 3 or 4. Alternatively, the isolated BRCA1 protein variant can be the protein variant isolated from a patient having Deletion No. 5. Or, the isolated BRCA1 protein variant can be the protein variant isolated from a patient having Deletion No. 6. Preferably the isolated BRCA1 protein variants contain at least 10, 20, 30, 40, 50 or 60 amino acid residues which encompass a BRCA1 variant amino acid sequences provided by SEQ ID NOs:10-14 and 83-93. Additionally, the isolated BRCA1 protein variants of the present invention may also include other amino acid variants, such as those created as a result of single nucleotide polymorphisms in the coding sequence of the BRCA1 gene.

It should be understood that hybrid proteins having one of the above mutant BRCA1 amino acid sequences and a non-BRCA1 amino acid sequence also fall within the scope of the present invention.

As will be apparent to a skilled artisan, the isolated nucleic acids and polypeptides of the present invention can be prepared using techniques generally known in the field of molecular biology. See generally, Sambrook et al., *Molecular Cloning: A Laboratory Manual*, $2^{nd}$ ed., Cold Spring Harbor Laboratory, Cold Spring Harbor, N.Y., 1989.

5. Antibodies

The present invention also provides antibodies selectively immunoreactive with an isolated BRCA1 protein variant of the present invention. As used herein, the term "antibody" encompasses both monoclonal and polyclonal antibodies that fall within any antibody classes, e.g., IgG, IgM, IgA, etc. The term "antibody" also includes antibody fragments including, but not limited to, Fab and $F(ab')_2$, conjugates of such fragments, and single-chain antibodies that can be made in accordance with U.S. Pat. No. 4,704,692, which is incorporated herein by reference. Specifically, as used herein, the phrase "selectively immunoreactive with an isolated BRCA1 protein variant of the present invention" means that the immunoreactivity of the antibody of the present invention with a BRCA1 protein variant of the present invention is substantially higher than that with a BRCA1 protein heretofore known in the art so that the binding of the antibody to the protein variant of the present invention is readily distinguishable from the binding of the antibody to the BRCA1 protein known in the art based on the strength of the binding affinities. Preferably, the binding constant differs by a magnitude of at least 2 fold, more preferably at least 5 fold, even more preferably at least 10 fold, and most preferably at least 100 fold.

To make the antibody, a BRCA1 protein variant of the present invention, or a suitable fragment thereof, can be used to immunize an animal. The BRCA1 protein variant can be made by any methods known in the art, e.g., by recombinant expression or chemical synthesis. Additionally, a mutant BRCA1 protein fragment having an amino acid sequence selected from SEQ ID NOs:10-14 or 83-93 can also be used. Preferably, the mutant BRCA1 protein fragment consists of less than 100 amino acids, more preferably less than 50 amino acids, and even more preferably less than 25 amino acids. As a result, a greater portion of the total antibodies may be selectively immunoreactive with a BRCA1 protein variant of the present invention. Techniques for immunizing animals for the purpose of making polyclonal antibodies are generally known in the art. See Harlow and Lane, *Antibodies: A Laboratory Manual*, Cold Spring Harbor Laboratory, Cold Spring Harbor, N.Y., 1988. A carrier may be necessary to increase the immunogenicity of the polypeptide. Suitable carriers known in the art include, but are not limited to, liposome, macromolecular protein or polysaccharide, or combination thereof. Preferably, the carrier has a molecular weight in the range of about 10,000 to 1,000,000. The polypeptide may also be administered along with an adjuvant, e.g., complete Freund's adjuvant.

The antibodies of the present invention preferably are monoclonal. Such monoclonal antibodies may be developed using any conventional techniques known in the art. For example, the popular hybridoma method disclosed in Kohler and Milstein, *Nature*, 256:495-497 (1975) is now a well-developed technique that can be used in the present invention. See U.S. Pat. No. 4,376,110, which is incorporated herein by reference. Essentially, B-lymphocytes producing a polyclonal antibody against a protein variant of the present invention can be fused with myeloma cells to generate a library of hybridoma clones. The hybridoma population is then screened for antigen binding specificity and also for immunoglobulin class (isotype). In this manner, pure hybridoma clones producing specific homogenous antibodies can be selected. See generally, Harlow and Lane, *Antibodies: A Laboratory Manual*, Cold Spring Harbor Press, 1988. Alternatively, other techniques known in the art may also be used to prepare monoclonal antibodies, which include but are not limited to the EBV hybridoma technique, the human N-cell hybridoma technique, and the trioma technique.

In addition, antibodies selectively immunoreactive with a protein variant of the present invention may also be recombinantly produced. For example, cDNAs prepared by PCR amplification from activated B-lymphocytes or hybridomas may be cloned into an expression vector to form a cDNA library, which is then introduced into a host cell for recombinant expression. The cDNA encoding a specific desired protein may then be isolated from the library. The isolated cDNA can be introduced into a suitable host cell for the expression of the protein. Thus, recombinant techniques can be used to recombinantly produce specific native antibodies, hybrid antibodies capable of simultaneous reaction with more than one antigen, chimeric antibodies (e.g., the constant and variable regions are derived from different sources), univalent antibodies which comprise one heavy and light chain pair coupled with the Fc region of a third (heavy) chain, Fab proteins, and the like. See U.S. Pat. No. 4,816,567; European Patent Publication No. 0088994; Munro, *Nature*, 312:597 (1984); Morrison, *Science*, 229: 1202 (1985); Oi et al., *BioTechniques*, 4:214 (1986); and Wood et al., *Nature*, 314:446-449 (1985), all of which are incorporated herein by reference. Antibody fragments such as Fv fragments, single-chain Fv fragments (scFv), Fab' fragments, and F(ab')$_2$ fragments can also be recombinantly produced by methods disclosed in, e.g., U.S. Pat. No. 4,946,778; Skerra & Plückthun, *Science*, 240:1038-1041 (1988); Better et al., *Science*, 240:1041-1043 (1988); and Bird, et al., *Science*, 242:423-426 (1988), all of which are incorporated herein by reference.

In a preferred embodiment, the antibodies provided in accordance with the present invention are partially or fully humanized antibodies. For this purpose, any methods known in the art may be used. For example, partially humanized chimeric antibodies having V regions derived from the tumor-specific mouse monoclonal antibody, but human C regions are disclosed in Morrison and Oi, *Adv. Immunol.*, 44:65-92 (1989). In addition, fully humanized antibodies can be made using transgenic non-human animals. For example, transgenic non-human animals such as transgenic mice can be produced in which endogenous immunoglobulin genes are suppressed or deleted, while heterologous antibodies are encoded entirely by exogenous immunoglobulin genes, preferably human immunoglobulin genes, recombinantly introduced into the genome. See e.g., U.S. Pat. Nos. 5,530,101; 5,545,806; 6,075,181; PCT Publication No. WO 94/02602; Green et. al., *Nat. Genetics*, 7: 13-21 (1994); and Lonberg et al., *Nature* 368: 856-859 (1994), all of which are incorporated herein by reference. The transgenic non-human host animal may be immunized with suitable antigens such as a protein variant of the present invention to illicit specific immune response thus producing humanized antibodies. In addition, cell lines producing specific humanized antibodies can also be derived from the immunized transgenic non-human animals. For example, mature B-lymphocytes obtained from a transgenic animal producing humanized antibodies can be fused to myeloma cells and the resulting hybridoma clones may be selected for specific humanized antibodies with desired binding specificities. Alternatively, cDNAs may be extracted from mature B-lymphocytes and used in establishing a library that is subsequently screened for clones encoding humanized antibodies with desired binding specificities. In addition, antibodies may also be produced in transgenic plants containing recombinant nucleic acids encoding antibodies.

In accordance with another embodiment of the present invention, a protein microchip or microarray is provided having (1) a BRCA1 protein variant of the present invention or a fragment thereof comprising an amino acid sequence according to SEQ ID NOs:10-14 or 83-93; and/or (2) an antibody selectively immunoreactive with a BRCA1 protein variant of the present invention.

Protein microarrays are becoming increasingly important in both proteomics research and protein-based detection and diagnosis of diseases. The protein microarrays in accordance with the present invention will be useful in a variety of applications including, e.g., high throughput screening for compounds capable of modulating the activities of a BRCA1 protein variant of the present invention. The protein microarrays are also useful in detecting the mutant BRCA1 proteins, and thus can be used in determining a predisposition to cancer, particularly breast cancer and ovarian cancer in patients.

The protein microarray of the present invention can be prepared by a number of methods known in the art. An example of a suitable method is that disclosed in MacBeath and Schreiber, *Science*, 289:1760-1763 (2000). Essentially, glass microscope slides are treated with an aldehyde-containing silane reagent (SuperAldehyde Substrates purchased from TeleChem International, Cupertino, Calif.). Nanoliter volumes of protein samples in a phophate-buffered saline with 40% glycerol are then spotted onto the treated slides using a high-precision contact-printing robot. After incubation, the slides are immersed in a bovine serum albumin (BSA)-containing buffer to quench the unreacted aldehydes and to form a BSA layer which functions to prevent non-specific protein binding in subsequent applications of the microchip. Alternatively, as disclosed in MacBeath and Schreiber, proteins or protein complexes of the present invention can be attached to a BSA-NHS slide by covalent linkages. BSA-NHS slides are fabricated by first attaching a molecular layer of BSA to the surface of glass slides and then activating the BSA with N,N'-disuccinimidyl carbonate. As a result, the amino groups of the lysine, aspartate, and glutamate residues on the BSA are activated and can form covalent urea or amide linkages with protein samples spotted on the slides. See MacBeath and Schreiber, *Science,* 289:1760-1763 (2000).

Another example of useful method for preparing the protein microchip of the present invention is that disclosed in PCT Publication Nos. WO 00/4389A2 and WO 00/04382, both of which are assigned to Zyomyx and are incorporated herein by reference. First, a substrate or chip base is covered with one or more layers of thin organic film to eliminate any surface defects, insulate proteins from the base materials, and to ensure a uniform protein array. Next, a plurality of protein-capturing agents (e.g., antibodies, peptides, etc.) are arrayed and attached to the base that is covered with the thin film. Proteins or protein complexes can then be bound to the capturing agents forming a protein microarray. The protein microchips are kept in flow chambers with an aqueous solution.

The protein microarray of the present invention can also be made by the method disclosed in PCT Publication No. WO 99/36576 assigned to Packard Bioscience Company, which is incorporated herein by reference. For example, a three-dimensional hydrophilic polymer matrix, i.e., a gel, is first deposited on a solid substrate such as a glass slide. The polymer matrix gel is capable of expanding or contracting and contains a coupling reagent that reacts with amine groups. Thus, proteins and protein complexes can be contacted with the matrix gel in an expanded aqueous and porous state to allow reactions between the amine groups on the protein or protein complexes with the coupling reagents thus immobilizing the proteins and protein complexes on the substrate. Thereafter, the gel is contracted to embed the attached proteins and protein complexes in the matrix gel.

Alternatively, the proteins and protein complexes of the present invention can be incorporated into a commercially available protein microchip, e.g., the ProteinChip System from Ciphergen Biosystems Inc., Palo Alto, Calif. The ProteinChip System comprises metal chips having a treated surface that interact with proteins. Basically, a metal chip surface is coated with a silicon dioxide film. The molecules of interest such as proteins and protein complexes can then be attached covalently to the chip surface via a silane coupling agent.

The protein microchips of the present invention can also be prepared with other methods known in the art, e.g., those disclosed in U.S. Pat. Nos. 6,087,102, 6,139,831, 6,087,103; PCT Publication Nos. WO 99/60156, WO 99/39210, WO 00/54046, WO 00/53625, WO 99/51773, WO 99/35289, WO 97/42507, WO 01/01142, WO 00/63694, WO 00/61806, WO 99/61148, WO 99/40434, all of which are incorporated herein by reference.

6. Genotyping

In another aspect of the present invention, methods are provided for predicting, in an individual, the likelihood of developing cancer. As described above, the large deletions in BRCA1 genes identified in accordance with the present invention are deleterious and predispose individuals having the deletions to cancer, particularly breast cancer and ovarian cancer. Thus, by detecting, in an individual, the presence or absence of one or more of the BRCA1 variants of the present invention, one can reasonably predict a predisposition to cancer, e.g., breast cancer and ovarian cancer.

Numerous techniques for detecting genetic variants are known in the art and can all be used for the method of this invention. The techniques can be nucleic acid-based or protein-based. In either case, the techniques used must be sufficiently sensitive so as to accurately detect the nucleotide or amino acid variations. Very often, a probe is utilized which is labeled with a detectable marker. Unless otherwise specified in a particular technique described below, any suitable marker known in the art can be used, including but not limited to, radioactive isotopes, fluorescent compounds, biotin which is detectable using strepavidin, enzymes (e.g., alkaline phosphatase), substrates of an enzyme, ligands and antibodies, etc. See Jablonski et al., *Nucleic Acids Res.,* 14:6115-6128 (1986); Nguyen et al., *Biotechniques,* 13:116-123 (1992); Rigby et al., *J. Mol. Biol.,* 113:237-251 (1977).

In a DNA-based detection method, a target DNA sample, i.e., a sample containing BRCA1 gene sequence should be obtained from the individual to be tested. Any tissue or cell sample containing the BRCA1 genomic DNA or mRNA, or a portion thereof, can be used. Preferably, a tissue sample containing cell nuclei and thus genomic DNA can be obtained from the individual. Blood samples can also be useful, except that only white blood cells and other lymphocytes have cell nuclei, while red blood cells are enucleated and contain mRNA. Nevertheless, mRNA is also useful as it can be analyzed for the presence of nucleotide variants in its sequence or serve as template for cDNA synthesis. The tissue or cell samples can be analyzed directly without much processing. Alternatively, nucleic acids including the target BRCA1 nucleic acids can be extracted, purified, or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

To determine the presence or absence of the deletion mutations identified in the present invention, one technique is simply sequencing the target BRCA1 genomic DNA or cDNA, particularly the region spanning the deletion locus to be detected. Various sequencing techniques are generally known and widely used in the art including the Sanger method and the Gilbert chemical method. The newly developed pyrosequencing method monitors DNA synthesis in real time using a luminometric detection system. Pyrosequencing has been shown to be effective in analyzing genetic polymorphisms such as single-nucleotide polymorphisms and can also be used in the present invention. See Nordstrom et al., *Biotechnol. Appl. Biochem.,* 31(2):107-112 (2000); Ahmadian et al., *Anal. Biochem.,* 280:103-110 (2000). For example, sequencing primers can be designed based on either mutant or wild-type BRCA1 gene intronic or exonic sequences such that the primers have the nucleotide sequence adjacent to a deletion locus identified in accordance with the present invention. In another example, PCR primers are designed based on either mutant or wild-type BRCA1 gene intronic or exonic sequences such that PCR amplification generates a BRCA1 DNA fragment spanning the deletion locus. As the large deletions identified in accordance with the present invention alter the size of the BRCA1 genomic DNA or cDNA, the presence or absence of a deletion mutation according to the present invention can be determined based on the molecular weight of the PCR amplification products generated using the PCR primers. Optionally, DNA sequencing is then performed on the amplified fragment to determine the nucleotide sequence of the suspect region.

Alternatively, the restriction fragment length polymorphism (RFLP) method may also prove to be a useful technique. In particular, the large deletions identified in accordance with the present invention result in the elimination and creation of restriction enzyme recognition sites.

Digestion of the mutant BRCA1 genomic DNAs or cDNAs with appropriate restriction enzyme(s) will generate restriction fragment length patterns distinct from those generated from wild-type BRCA1 genomic DNA or cDNA. Thus, the large deletions in BRCA1 of the present invention can be detected by RFLP. The application of the RFLP techniques known in the art to the present invention will be apparent to skilled artisans.

Similarly, genomic DNA can be obtained from a patient sample and digested by appropriate restriction enzyme(s). Southern blot can be performed using a probe having a wild-type BRCA1 sequence that is missing from one or more of the BRCA1 genetic variants of the present invention. Alternatively, probes specific to the mutant BRCA1 nucleic acids of the present invention can also be used.

The presence or absence of a BRCA1 deletion mutation identified according to the present invention can also be detected using the amplification refractory mutation system (ARMS) technique. See e.g., European Patent No. 0,332, 435; Newton et al., *Nucleic Acids Res.*, 17:2503-2515 (1989); Fox et al., *Br. J. Cancer*, 77:1267-1274 (1998); Robertson et al., *Eur. Respir. J.*, 12:477-482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques developed in the past few years can be used. See e.g., Gibson et al., *Clin. Chem.* 43:1336-1341 (1997). Thus, for example, primers having a sequence selected from SEQ ID NOs:42-47, 53-63, and 70-79 can all be useful in this technique.

Similar to the ARMS technique is the mini sequencing or single nucleotide primer extension method, which is based on the incorporation of a single nucleotide. An oligonucleotide primer matching the nucleotide sequence immediately 5' to the locus being tested is hybridized to the target DNA or mRNA in the presence of labeled dideoxyribonucleotides. A labeled nucleotide is incorporated or linked to the primer only when the dideoxyribonucleotides matches the nucleotide at the variant locus being detected. Thus, the identity of the nucleotide at the variant locus can be revealed based on the detection label attached to the incorporated dideoxyribonucleotides. See Syvanen et al., *Genomics*, 8:684-692 (1990); Shumaker et al., *Hum. Mutat.*, 7:346-354 (1996); Chen et al., *Genome Res.*, 10:549-547 (2000).

Another set of techniques useful in the present invention is the so-called "oligonucleotide ligation assay" (OLA) in which differentiation between a wild-type locus and a mutation is based on the ability of two oligonucleotides to anneal adjacent to each other on the target DNA molecule allowing the two oligonucleotides joined together by a DNA ligase. See Landergren et al., *Science*, 241:1077-1080 (1988); Chen et al, *Genome Res.*, 8:549-556 (1998); Iannone et al., *Cytometry*, 39:131-140 (2000). Thus, for example, to detect a mutation at a particular locus in the BRCA1 gene, two oligonucleotides can be synthesized, one having the BRCA1 sequence just 5' upstream from the locus with its 3' end nucleotide being identical to the nucleotide in the mutant locus of the BRCA1 gene, the other having a nucleotide sequence matching the BRCA1 sequence immediately 3' downstream from the locus in the BRCA1 gene. The oligonucleotides can be labeled for the purpose of detection. Upon hybridizing to the target BRCA1 gene under a stringent condition, the two oligonucleotides are subjected to ligation in the presence of a suitable ligase. The ligation of the two oligonucleotides would indicate that the target DNA has a nucleotide variant at the locus being detected. Thus, for example, oligonucleotides can be readily designed based on the deletion loci present in mutant BRCA1 genomic DNA or cDNA sequences that result from Deletion Nos. 1, 2, 3, 4, 5, or 6.

Detection of the genetic variations identified in accordance with the present invention can also be accomplished by a variety of hybridization-based approaches. Allele-specific oligonucleotides are useful. See Conner et al., *Proc. Natl. Acad. Sci. USA*, 80:278-282 (1983); Saiki et al, *Proc. Natl. Acad. Sci. USA*, 86:6230-6234 (1989). Oligonucleotide probes hybridizing specifically to a BRCA1 gene allele having a particular gene variant at a particular locus but not to other alleles can be designed by methods known in the art. The probes can have a length of, e.g., from 10 to about 50 nucleotide bases. The target BRCA1 genomic DNA or cDNA and the oligonucleotide probe can be contacted with each other under conditions sufficiently stringent such that the genetic variant can be distinguished from the wild-type BRCA1 gene based on the presence or absence of hybridization. The probe can be labeled to provide detection signals. Alternatively, the allele-specific oligonucleotide probe can be used as a PCR amplification primer in an "allele-specific PCR" and the presence or absence of a PCR product of the expected length would indicate the presence or absence of a particular genetic variant. In this respect, oligos having a sequence selected from SEQ ID NOs:7-9, 15-79 and 81 can be used.

Another useful technique that is gaining increased popularity is mass spectrometry. See Graber et al., *Curr. Opin. Biotechnol.*, 9:14-18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucelotides and dideoxyribonucleotides. The resulting mixture of newly extended primers is then analyzed by MALDI-TOF. See e.g., Monforte et al., *Nat. Med.*, 3:360-362 (1997). In another example, primers can be designed based on either mutant or wild-type BRCA1 gene intronic or exonic sequences such that the primers have the nucleotide sequences adjacent to and flanking a deletion locus identified in accordance with the present invention. PCR amplification on a patient sample is carried out using the primers. Mass spectrometry is then performed on the PCR product.

In addition, the microchip or microarray technologies are also applicable to the detection method of the present invention. Essentially, in microchips, a large number of different oligonucleotide probes are immobilized in an array on a substrate or carrier, e.g., a silicon chip or glass slide. Target nucleic acid sequences to be analyzed can be contacted with the immobilized oligonucleotide probes on the microchip. See Lipshutz et al., *Biotechniques*, 19:442-447

(1995); Chee et al., *Science*, 274:610-614 (1996); Kozal et al., *Nat. Med.* 2:753-759 (1996); Hacia et al., *Nat. Genet.*, 14:441-447 (1996); Saiki et al., *Proc. Natl. Acad. Sci. USA*, 86:6230-6234 (1989); Gingeras et al., *Genome Res.*, 8:435-448 (1998). Alternatively, the multiple target nucleic acid sequences to be studied are fixed onto a substrate and an array of probes is contacted with the immobilized target sequences. See Drmanac et al., *Nat. Biotechnol.*, 16:54-58 (1998). Numerous microchip technologies have been developed incorporating one or more of the above described techniques for detecting mutations particularly SNPs. The microchip technologies combined with computerized analysis tools allow fast screening in a large scale. The adaptation of the microchip technologies to the present invention will be apparent to a person of skill in the art apprised of the present disclosure. See, e.g., U.S. Pat. No. 5,925,525 to Fodor et al; Wilgenbus et al., *J. Mol. Med.*, 77:761-786 (1999); Graber et al., *Curr. Opin. Biotechnol.*, 9:14-18 (1998); Hacia et al., *Nat. Genet.*, 14:441-447 (1996); Shoemaker et al., *Nat. Genet.*, 14:450-456 (1996); DeRisi et al., *Nat. Genet.*, 14:457-460 (1996); Chee et al., *Nat. Genet.*, 14:610-614 (1996); Lockhart et al., *Nat. Genet.*, 14:675-680 (1996); Drobyshev et al., *Gene*, 188:45-52 (1997).

As is apparent from the above survey of the suitable detection techniques, it may or may not be necessary to amplify the target DNA, i.e., the BRCA1 genomic DNA or cDNA sequence to increase the number of target DNA molecules, depending on the detection techniques used. For example, most PCR-based techniques combine the amplification of a portion of the target and the detection of mutations. PCR amplification is well known in the art and is disclosed in U.S. Pat. Nos. 4,683,195 and 4,800,159, both of which are incorporated herein by reference. For non-PCR-based detection techniques, if necessary, the amplification can be achieved by, e.g., in vivo plasmid multiplication, or by purifying the target DNA from a large amount of tissue or cell samples. See generally, Sambrook et al., *Molecular Cloning: A Laboratory Manual*, $2^{nd}$ ed., Cold Spring Harbor Laboratory, Cold Spring Harbor, N.Y., 1989. However, even with scarce samples, many sensitive techniques have been developed in which genetic variations can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., *J. Clin. Microbiol.*, 34:901-907 (1996); Collins et al., *Nucleic Acids Res.*, 25:2979-2984 (1997); Horn et al., *Nucleic Acids Res.*, 25:4835-4841 (1997); Horn et al., *Nucleic Acids Res.*, 25:4842-4849 (1997); Nilsen et al., *J. Theor. Biol.*, 187:273-284 (1997).

A number of other techniques that avoid amplification all together include, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See Graham et al., *Anal. Chem.*, 69:4703-4707 (1997). The fluorescence correlation spectroscopy is based on the spatio-temporal correlations between fluctuating light signals and trapping single molecules in an electric field. See Eigen et al., *Proc. Natl. Acad. Sci. USA*, 91:5740-5747 (1994). In single-molecule electrophoresis, the electrophoretic velocity of a fluorescently tagged nucleic acid is determined by measuring the time required for the molecule to travel a predetermined distance between two laser beams. See Castro et al., *Anal. Chem.*, 67:3181-3186 (1995). Additionally, the Invader assay and the rolling circle amplification technique may also be used. See e.g. Lyamichev et al., *Nat. Biotechnol.*, 17:292-296 (1999); Lizardi et al., *Nature Genetics*, 19:225-232 (1998).

In addition, the allele-specific oligonucleotides (ASO) can also be used in in situ hybridization using tissues or cells as samples. The oligonucleotide probes which can hybridize differentially with the wild-type gene sequence or the gene sequence harboring a mutation may be labeled with radioactive isotopes, fluorescence, or other detectable markers. In situ hybridization techniques are well known in the art and their adaptation to the present invention for detecting the presence or absence of a genetic variant in the BRCA1 gene of a particular individual should be apparent to a skilled artisan apprised of this disclosure.

Protein-based detection techniques may also prove to be useful, especially when the genetic variant causes amino acid substitutions or deletions or insertions that affect the protein primary, secondary or tertiary structure. To detect the amino acid variations, protein sequencing techniques may be used. For example, a BRCA1 protein or fragment thereof can be synthesized by recombinant expression using a BRCA1 DNA fragment isolated from an individual to be tested. Preferably, a BRCA1 cDNA fragment of no more than 100 to 150 base pairs encompassing the polymorphic locus to be determined is used. The amino acid sequence of the peptide can then be determined by conventional protein sequencing methods. Alternatively, the recently developed HPLC-microscopy tandem mass spectrometry technique can be used for determining the amino acid sequence variations. In this technique, proteolytic digestion is performed on a protein, and the resulting peptide mixture is separated by reversed-phase chromatographic separation. Tandem mass spectrometry is then performed and the data collected therefrom is analyzed. See Gatlin et al., *Anal. Chem.*, 72:757-763 (2000).

Other useful protein-based detection techniques include immunoaffinity assays based on antibodies selectively immunoreactive with mutant BRCA1 proteins according to the present invention. Such antibodies may react specifically with epitopes comprising the polypeptide fragments spanning the junction regions of BRCA1 proteins that correspond to deletion loci in the mutant BRCA1 mRNAs transcribed from the mutant BRCA1 genomic DNAs of the present invention (i.e., the deletion loci of variant BRCA1 polypeptides produced as a result of Deletion Nos. 1-6. Alternatively, such antibodies may react specifically with epitopes present on the novel carboxyl-terminal polypeptides of the BRCA1 protein variants resulting from Deletion Nos. 5 and 6. Methods for producing such antibodies are described above in detail. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. Other well known antibody-based techniques can also be used including, e.g., enzyme-linked immunosorbent assay (ELISA), radioimmunoassay (RIA), immunoradiometric assays (IRMA) and immunoenzymatic assays (IEMA), including sandwich assays using monoclonal or polyclonal antibodies. See e.g., U.S. Pat. Nos. 4,376,110 and 4,486,530, both of which are incorporated herein by reference.

It is noted that heterozygotes of the BRCA1 genetic variants of the present invention are predisposed to cancer such as breast cancer and ovarian cancer. That is, as long as an individual has one chromosome containing a BRCA1 genetic variant of the present invention, there is an increased likelihood of breast cancer and/or ovarian cancer in the individual.

Thus, various techniques can be used in genotyping a BRCA1 gene of an individual to determine, in the individual, the presence or absence of a BRCA1 genetic variant selected from the group consisting of Deletion Nos. 1 to 6. Typically, once the presence or absence of a BRCA 1 genetic variant of the present invention is determined, the result can be cast in a communicable form that can be communicated to the individual patient. Such a form can vary and can be tangible or intangible. The result with regard to the presence or absence of a BRCA1 genetic variant of the present invention in the individual tested can be embodied in descriptive statements, diagrams, photographs, charts, images or any other visual forms. For example, images of gel electrophoresis of PCR products can be used in explaining the results. Diagrams showing where a deletion occurs in an individual's BRCA1 gene are also useful in communicating the test results. The statements and visual forms can be recorded on a tangible media such as papers, computer readable media such as floppy disks, compact disks, etc., or on an intangible media, e.g., an electronic media in the form of e-mail, or on a preferably secured website on the internet or an intranet. In addition, the result with regard to the presence or absence of a BRCA1 genetic variant of the present invention in the individual tested can also be recorded in a sound form and transmitted through any suitable media, e.g., analog or digital cable lines, fiber optic cables, etc., via telephone, facsimile, wireless mobile phone, internet phone and the like.

The present invention also provides kits for practicing the genotyping methods described above. The kits may include a carrier for the various components of the kit. The carrier can be a container or support, in the form of, e.g., bag, box, tube, rack, and is optionally compartmentalized. The carrier may define an enclosed confinement for safety purposes during shipment and storage. The kit also includes various components useful in detecting nucleotide or amino acid variants discovered in accordance with the present invention using the above-discussed detection techniques.

In one embodiment, the detection kit includes one or more oligonucleotides useful in detecting the genetic variants in BRCA1 gene sequence in accordance with the present invention. Preferably, the oligonucleotides are designed such that they are specific to a BRCA1 nucleic acid variant of the present invention under stringent conditions. That is, the oligonucleotides should be designed such that it can be used in distinguishing one genetic variant from another at a particular locus under predetermined stringent hybridization conditions. Examples of such oligonucleotides include nucleic acids having a sequence selected from SEQ ID NOs:7-9, 15-79 and 81. Thus, the oligonucleotides can be used in mutation-detecting techniques such as allele-specific oligonucleotides (ASO), allele-specific PCR, TaqMan-based quantitative PCR, chemiluminescence-based techniques, molecular beacons, and improvements or derivatives thereof, e.g., microchip technologies.

In another embodiment of this invention, the kit includes one or more oligonucleotides suitable for use in detecting techniques such as ARMS, oligonucleotide ligation assay (OLA), and the like. For example, the oligonucleotides in this embodiment include a BRCA1 gene sequence immediately 5' upstream from a deletion locus to be analyzed. The 3' end nucleotide of the oligo is the first nucleotide on the 3' side of the deletion locus. Examples of suitable oligos include, but are not limited to, those consisting of a sequence selected from SEQ ID NOs:1, 3, 5, 6, 42-47, 53-63, and 73-79.

The oligonucleotides in the detection kit can be labeled with any suitable detection marker including but not limited to, radioactive isotopes, fluorophores, biotin, enzymes (e.g., alkaline phosphatase), enzyme substrates, ligands and antibodies, etc. See Jablonski et al., *Nucleic Acids Res.*, 14:6115-6128 (1986); Nguyen et al., *Biotechniques,* 13:116-123 (1992); Rigby et al., *J. Mol. Biol.,* 113:237-251 (1977). Alternatively, the oligonucleotides included in the kit are not labeled, and instead, one or more markers are provided in the kit so that users may label the oligonucleotides at the time of use.

In another embodiment of the invention, the detection kit contains one or more antibodies selectively immunoreactive with a BRCA1 protein variant of the present invention. Methods for producing and using such antibodies have been described above in detail.

Various other components useful in the detection techniques may also be included in the detection kit of this invention. Examples of such components include, but are not limited to, DNA polymerase, reverse transcriptase, deoxyribonucleotides, dideoxyribonucleotides other primers suitable for the amplification of a target DNA or mRNA sequence, RNase A, mutS protein, and the like. In addition, the detection kit preferably includes instructions on using the kit for detecting genetic variants in BRCA1 gene sequences, particularly the genetic variants of the present invention.

7. Screening Assays

The present invention further provides a method for identifying compounds capable of modulating, preferably enhancing the activities of a BRCA1 protein variant of the present invention. Such compounds may prove to be useful in treating or preventing symptoms associated with decreased BRCA1 protein activities, e.g., cancer. For this purpose, a mutant BRCA1 protein or fragment thereof containing a particular deletion in accordance with the present invention can be used in any of a variety of drug screening techniques. Drug screening can be performed as described herein or using well known techniques, such as those described in U.S. Pat. Nos. 5,800,998 and 5,891,628, both of which are incorporated herein by reference. The candidate therapeutic compounds may include, but are not limited to proteins, small peptides, nucleic acids, and analogs thereof. Preferably, the compounds are small organic molecules having a molecular weight of no greater than 10,000 dalton, more preferably less than 5,000 dalton.

In one embodiment of the present invention, the method is primarily based on binding affinities to screen for compounds capable of interacting with or binding to a BRCA1 protein variant. Compounds to be screened may be peptides or derivatives or mimetics thereof, or non-peptide small molecules. Conveniently, commercially available combinatorial libraries of compounds or phage display libraries displaying random peptides are used.

Various screening techniques known in the art may be used in the present invention. The BRCA1 protein variants (drug target) can be prepared by any suitable methods, e.g., by recombinant expression and purification. The polypeptide or fragment thereof may be free in solution but preferably is immobilized on a solid support, e.g., in a protein microchip, or on a cell surface. Various techniques for immobilizing proteins on a solid support are known in the art. For example, PCT Publication WO 84/03564 discloses synthesizing a large numbers of small peptide test compounds on a solid substrate, such as plastic pins or other surfaces. Alternatively, purified mutant BRCA1 protein, or fragments thereof, can be coated directly onto plates such as multi-well plates. Non-neutralizing antibodies, i.e., antibodies capable binding to the BRCA1 protein, or fragments thereof, that do not substantially affect its biological activities may also be used for immobilizing the BRCA1 protein, or fragments thereof, on a solid support.

To affect the screening, test compounds can be contacted with the immobilized BRCA1 protein, or fragments thereof, to allow binding to occur and complexes to form under standard binding conditions. Either the drug target or test compounds are labeled with a detectable marker using well known labeling techniques. To identify binding compounds, one may measure the steady state or end-point formation of the drug target-test compound complexes, or kinetics for the formation thereof.

Alternatively, a known ligand capable of binding to the drug target can be used in competitive binding assays. Complexes between the known ligand and the drug target can be formed and then contacted with test compounds. The ability of a test compound to interfere with the interaction between the drug target and the known ligand is measured using known techniques. One exemplary ligand is an antibody capable of specifically binding the drug target. Particularly, such an antibody is especially useful for identifying peptides that share one or more antigenic determinants of the BRCA1 protein, or fragments thereof, and preferably antigenic determinants specific to the BRCA1 protein variants of the present invention.

In another embodiment, a yeast two-hybrid system may be employed to screen for proteins or small peptides capable of interacting with a BRCA1 protein variant. For example, a battery of fusion proteins each containing a random small peptide fused to e.g., Gal 4 activation domain, can be co-expressed in yeast cells with a fusion protein having the Gal 4 binding domain fused to a BRCA1 protein variant. In this manner, small peptides capable of interacting with the BRCA1 protein variant can be identified. Alternatively, compounds can also be tested in a yeast two-hybrid system to determine their ability to inhibit the interaction between the BRCA1 protein variant and a known protein, which is known to interact with the BRCA1 protein or polypeptide or fragment thereof. Again, one example of such proteins is an antibody specifically against the BRCA1 protein variant. Yeast two-hybrid systems and use thereof are generally known in the art and are disclosed in, e.g., Bartel et al., in: *Cellular Interactions in Development: A Practical Approach*, Oxford University Press, pp. 153-179 (1993); Fields and Song, *Nature*, 340:245-246 (1989); Chevray and Nathans, *Proc. Natl. Acad. Sci. USA*, 89:5789-5793 (1992); Lee et al., *Science*, 268:836-844 (1995); and U.S. Pat. Nos. 6,057,101, 6,051,381, and 5,525,490, all of which are incorporated herein by reference.

The compounds thus identified can be further tested for activities, e.g., in stimulating the mutant BRCA1's biological activities, e.g., in DNA repair and in interacting with its known interacting partner proteins.

Once an effective compound is identified, structural analogs or mimetics thereof can be produced based on rational drug design with the aim of improving drug efficacy and stability, and reducing side effects. Methods known in the art for rational drug design can be used in the present invention. See, e.g., Hodgson et al., *Bio/Technology*, 9:19-21 (1991); U.S. Pat. Nos. 5,800,998 and 5,891,628, all of which are incorporated herein by reference. An example of rational drug design is the development of HIV protease inhibitors. See Erickson et al., *Science*, 249:527-533 (1990). Preferably, rational drug design is based on one or more compounds selectively binding to a mutant BRCA1 protein or a fragment thereof.

In one embodiment, the three-dimensional structure of, e.g., a BRCA1 protein variant, is determined by biophysical techniques such as X-ray crystallography, computer modeling, or both. Desirably, the structure of the complex between an effective compound and the mutant BRCA1 protein is determined, and the structural relationship between the compound and the protein is elucidated. In this manner, the moieties and the three-dimensional structure of the selected compound, i.e., lead compound, critical to the its binding to the mutant BRCA1 protein are revealed. Medicinal chemists can then design analog compounds having similar moieties and structures. In addition, the three-dimensional structure of wild-type BRCA1 protein is also desirably deciphered and compared to that of a mutant BRCA1 protein. This will aid in designing compounds selectively interacting with the mutant BRCA1 protein.

In another approach, a selected peptide compound capable of binding the BRCA1 protein variant can be analyzed by alanine scanning mutagenesis. See Wells, et al., *Methods Enzymol.*, 202:301-306 (1991). In this technique, an amino acid residue of the peptide is replaced by Alanine, and its effect on the peptide's binding affinity to the mutant BRCA1 protein is tested. Amino acid residues of the selected peptide are analyzed in this manner to determine the domains or residues of the peptide important to its binding to mutant BRCA1 protein. These residues or domains constituting the active region of the compound are known as its "pharmacophore". This information can be very helpful in rationally designing improved compounds.

Once the pharmacophore has been elucidated, a structural model can be established by a modeling process which may include analyzing the physical properties of the pharmacophore such as stereochemistry, charge, bonding, and size using data from a range of sources, e.g., NMR analysis, x-ray diffraction data, alanine scanning, and spectroscopic techniques and the like. Various techniques including computational analysis, similarity mapping and the like can all be used in this modeling process. See e.g., Perry et al., in *OSAR: Quantitative Structure-Activity Relationships in Drug Design*, pp. 189-193, Alan R. Liss, Inc., 1989; Rotivinen et al., *Acta Pharmaceutical Fennica*, 97:159-166 (1988); Lewis et al., *Proc. R. Soc. Lond.*, 236:125-140 (1989); McKinaly et al., *Annu. Rev. Pharmacol. Toxiciol.*, 29:111-122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effect can be developed.

8. Cell and Animal Models

In yet another aspect of the present invention, a cell line and a transgenic animal carrying a BRCA1 nucleic acid variant in accordance with the present invention are provided. The cell line and transgenic animal can be used as model systems for studying cancers and testing various therapeutic approaches in treating cancers, e.g., breast cancer and ovarian cancer.

To establish the cell line, cells expressing the mutant BRCA1 protein can be isolated from an individual carrying the genetic variants. The primary cells can be transformed or immortalized using techniques known in the art. Alternatively, normal cells expressing a wild-type BRCA1 protein or other type of genetic variants can be manipulated to replace the entire endogenous BRCA1 gene with a BRCA1 nucleic acid variant of the present invention, or simply to introduce mutations into the endogenous BRCA1 gene. The genetically engineered cells can further be immortalized.

A more valuable model system is a transgenic animal. A transgenic animal can be made by replacing its endogenous BRCA1 gene ortholog with a human BRCA1 nucleic acid variant of the present invention. Alternatively, deletions can be introduced into the endogenous animal BRCA1 gene ortholog to simulate the BRCA1 alleles discovered in accordance with the present invention. Techniques for making such transgenic animals are well known and are described in, e.g., Capecchi, et al., *Science,* 244:1288 (1989); Hasty et al., *Nature,* 350:243 (1991); Shinkai et al., *Cell,* 68:855 (1992); Mombaerts et al., *Cell,* 68:869 (1992); Philpott et al., *Science,* 256:1448 (1992); Snouwaert et al., *Science,* 257: 1083 (1992); Donehower et al., *Nature,* 356:215 (1992); Hogan et al., *Manipulating the Mouse Embryo; A Laboratory Manual,* $2^{nd}$ edition, Cold Spring Harbor Laboratory Press, 1994; and U.S. Pat. Nos. 5,800,998, 5,891,628, and 4,873,191, all of which are incorporated herein by reference.

The cell line and transgenic animal are valuable tools for studying the mutant BRCA1 genes, and in particular for testing in vivo the compounds identified in the screening method of this invention and other therapeutic approaches as discussed above. As is well known in the art, studying drug candidates in a suitable animal model before advancing them into human clinical trials is particularly important because not only can efficacy of the drug candidates can be confirmed in the model animal, but the toxicology profiles, side effects, and dosage ranges can also be determined. Such information is then used to guide human clinical trials.

Although the foregoing invention has been described in some detail by way of illustration and example for purposes of clarity of understanding, it will be obvious that certain changes and modifications may be practiced within the scope of the appended claims.

All publications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. An isolated nucleic acid comprising SEQ ID NO:6, and the complement thereof.

2. The isolated nucleic acid of claim 1, wherein said isolated nucleic acid comprises SEQ ID NO:37, or the complement thereof.

3. A method of making the isolated nucleic acid of claim 2 comprising amplifying genomic DNA isolated from a sample obtained from a human patient.

4. A method of making the isolated nucleic acid of claim 1 comprising amplifying genomic DNA isolated from a sample obtained from a human patient.

5. The method of claim 4, wherein said sample is a blood sample.

6. The method of claim 4, wherein said amplification is by the polymerase chain reaction.

7. The method of claim 4, wherein said patient is being evaluated for an enhanced risk of cancer.

8. The method of claim 4, wherein said cancer is breast or ovarian cancer.

9. The isolated nucleic acid of claim 1, wherein said isolated nucleic acid comprises SEQ ID NO:38, or the complement thereof.

10. The isolated nucleic acid of claim 2, wherein said isolated nucleic acid is a BRCA1 nucleic acid comprising SEQ ID NO:37.

11. A method of making the isolated nucleic acid of claim 9 comprising amplifying genomic DNA isolated from a sample obtained from a human patient.

12. The isolated nucleic acid of claim 1, wherein said isolated nucleic acid comprises SEQ ID NO:39, or the complement thereof.

13. The isolated nucleic acid of claim 9, wherein said isolated nucleic acid is a BRCA1 nucleic acid comprising SEQ ID NO:38.

14. A method of making the isolated nucleic acid of claim 12 comprising amplifying genomic DNA isolated from a sample obtained from a human patient.

15. The isolated nucleic acid of claim 1, wherein said isolated nucleic acid comprises SEQ ID NO:40, or the complement thereof.

16. The isolated nucleic acid of claim 12, wherein said isolated nucleic acid is a BRCA1 nucleic acid comprising SEQ ID NO:39.

17. A method of making the isolated nucleic acid of claim 15 comprising amplifying genomic DNA isolated from a sample obtained from a human patient.

18. The isolated nucleic acid of claim 1, wherein said isolated nucleic acid comprises SEQ ID NO:41, or the complement thereof.

19. A method of making the isolated nucleic acid of claim 18 comprising amplifying genomic DNA isolated from a sample obtained from a human patient.

20. The isolated nucleic acid of claim 1, wherein said isolated nucleic acid is a BRCA1 nucleic acid comprising SEQ ID NO:6.

* * * * *

SEQUENCE LISTING

```
<160> NUMBER OF SEQ ID NOS: 93

<210> SEQ ID NO 1
<211> LENGTH: 42
<212> TYPE: DNA
<213> ORGANISM: Homo sapiens

<400> SEQUENCE: 1
tctcggcctc ccaaagtgct gggattacag gtgtgagcca tc                         42

<210> SEQ ID NO 2
<211> LENGTH: 13
<212> TYPE: DNA
<213> ORGANISM: Homo sapiens

<400> SEQUENCE: 2
tcaaaaaaaa ata                                                         13

<210> SEQ ID NO 3
<211> LENGTH: 42
<212> TYPE: DNA
<213> ORGANISM: Homo sapiens

<400> SEQUENCE: 3
tgtaatccca gcactttggg aggccgaggc gggcagatca ca                         42

<210> SEQ ID NO 4
<211> LENGTH: 10
<212> TYPE: DNA
<213> ORGANISM: Homo sapiens
```

-continued

```
<400> SEQUENCE: 4
ttcagtgacc                                                            10

<210> SEQ ID NO 5
<211> LENGTH: 48
<212> TYPE: DNA
<213> ORGANISM: Homo sapiens

<400> SEQUENCE: 5
gtaatcccag ctactcagga ggctgaggca ggagaattgc ttgaaccc                  48

<210> SEQ ID NO 6
<211> LENGTH: 56
<212> TYPE: DNA
<213> ORGANISM: Homo sapiens

<400> SEQUENCE: 6
gggaggctaa ggcaggagaa tcgcttgaac ctggaggcag aggttgcagt gagccc         56

<210> SEQ ID NO 7
<211> LENGTH: 8
<212> TYPE: DNA
<213> ORGANISM: Homo sapiens

<400> SEQUENCE: 7 ctagatgc                                                              8

<210> SEQ ID NO 8
<211> LENGTH: 8
<212> TYPE: DNA
<213> ORGANISM: Homo sapiens

<400> SEQUENCE: 8 aagatgc                                                               8

<210> SEQ ID NO 9
<211> LENGTH: 8
<212> TYPE: DNA
<213> ORGANISM: Homo sapiens

<400> SEQUENCE: 9 aaagatct                                                              8

<210> SEQ ID NO 10
<211> LENGTH: 7
<212> TYPE: PRT
<213> ORGANISM: Homo sapiens

<400> SEQUENCE: 10

Gln Asp Leu Asp Ala Glu Phe
1               5

<210> SEQ ID NO 11
<211> LENGTH: 7
<212> TYPE: PRT
<213> ORGANISM: Homo sapiens

<400> SEQUENCE: 11

Gly Val Glu Arg Cys Ser Cys
1               5

<210> SEQ ID NO 12
<211> LENGTH: 7
```

```
<212> TYPE: PRT
<213> ORGANISM: Homo sapiens

<400> SEQUENCE: 12

Ser Glu Lys Asp Leu Gln Gly
1               5

<210> SEQ ID NO 13
<211> LENGTH: 13
<212> TYPE: PRT
<213> ORGANISM: Homo sapiens

<400> SEQUENCE: 13

Cys Ser Cys Thr Ser Gly Pro Glu Asn Thr Thr Ser Leu
1               5                   10

<210> SEQ ID NO 14
<211> LENGTH: 69
<212> TYPE: PRT
<213> ORGANISM: Homo sapiens

<400> SEQUENCE: 14

Asp Leu Gln Gly Ala Arg Asn Leu Leu Leu Trp Ala Leu His Gln His
1               5                   10                  15

Ala His Arg Ser Thr Gly Met Asp Gly Thr Ala Val Trp Cys Phe Cys
                20                  25                  30

Gly Glu Gly Ala Phe Ile Ile His Pro Trp His Arg Cys Pro Pro Asn
            35                  40                  45

Cys Gly Cys Ala Ala Arg Cys Leu Asp Arg Gly Gln Trp Leu Pro Cys
    50                  55                  60

Asn Trp Ala Asp Val
65

<210> SEQ ID NO 15
<211> LENGTH: 49
<212> TYPE: DNA
<213> ORGANISM: Homo sapiens

<400> SEQUENCE: 15
cccgtctcgg cctcccaaag tgctgggatt acaggtgtga gccatcgcg            49

<210> SEQ ID NO 16
<211> LENGTH: 60
<212> TYPE: DNA
<213> ORGANISM: Homo sapiens

<400> SEQUENCE: 16
atccacccgt ctcggcctcc caaagtgctg ggattacagg tgtgagccat cgcgcctagc   60

<210> SEQ ID NO 17
<211> LENGTH: 79
<212> TYPE: DNA
<213> ORGANISM: Homo sapiens

<400> SEQUENCE: 17
tgacctcgtg atccacccgt ctcggcctcc caaagtgctg ggattacagg tgtgagccat   60
cgcgcctagc ctatgatga                                                79

<210> SEQ ID NO 18
<211> LENGTH: 15
<212> TYPE: DNA
<213> ORGANISM: Homo sapiens
```

```
<400> SEQUENCE: 18
ctcaaaaaaa aatac                                            15

<210> SEQ ID NO 19
<211> LENGTH: 20
<212> TYPE: DNA
<213> ORGANISM: Homo sapiens

<400> SEQUENCE: 19
catctcaaaa aaaatacat                                        20

<210> SEQ ID NO 20
<211> LENGTH: 26
<212> TYPE: DNA
<213> ORGANISM: Homo sapiens

<400> SEQUENCE: 20
actccatctc aaaaaaaaat acataa                                26

<210> SEQ ID NO 21
<211> LENGTH: 30
<212> TYPE: DNA
<213> ORGANISM: Homo sapiens

<400> SEQUENCE: 21
actccatctc aaaaaaaaat acataaattg                            30

<210> SEQ ID NO 22
<211> LENGTH: 39
<212> TYPE: DNA
<213> ORGANISM: Homo sapiens

<400> SEQUENCE: 22
actccatctc aaaaaaaaat acataaattg gctgggcgt                  39

<210> SEQ ID NO 23
<211> LENGTH: 49
<212> TYPE: DNA
<213> ORGANISM: Homo sapiens

<400> SEQUENCE: 23
acagagcaag actccatctc aaaaaaaaat acataaattg gctgggcgt       49

<210> SEQ ID NO 24
<211> LENGTH: 44
<212> TYPE: DNA
<213> ORGANISM: Homo sapiens

<400> SEQUENCE: 24
ctgtaatccc agcactttgg gaggccgagg cgggcagatc acaa            44

<210> SEQ ID NO 25
<211> LENGTH: 49
<212> TYPE: DNA
<213> ORGANISM: Homo sapiens

<400> SEQUENCE: 25
gcctgtaatc ccagcacttt gggaggccga ggcgggcaga tcacaaggt       49

<210> SEQ ID NO 26
<211> LENGTH: 60
<212> TYPE: DNA
```

<213> ORGANISM: Homo sapiens

<400> SEQUENCE: 26
gcttacgcct gtaatcccag cactttggga ggccgaggcg ggcagatcac aaggtcagga    60

<210> SEQ ID NO 27
<211> LENGTH: 80
<212> TYPE: DNA
<213> ORGANISM: Homo sapiens

<400> SEQUENCE: 27
gtggtgggtg gcttacgcct gtaatcccag cactttggga ggccgaggcg ggcagatcac    60
aaggtcagga gttcgagacc                                                80

<210> SEQ ID NO 28
<211> LENGTH: 17
<212> TYPE: DNA
<213> ORGANISM: Homo sapiens

<400> SEQUENCE: 28
gaggtttcag tgaccca                                                   17

<210> SEQ ID NO 29
<211> LENGTH: 19
<212> TYPE: DNA
<213> ORGANISM: Homo sapiens

<400> SEQUENCE: 29
cagaggtttc agtgaccca                                                 19

<210> SEQ ID NO 30
<211> LENGTH: 26
<212> TYPE: DNA
<213> ORGANISM: Homo sapiens

<400> SEQUENCE: 30
gcagaggttt cagtgaccca agatcg                                         26

<210> SEQ ID NO 31
<211> LENGTH: 30
<212> TYPE: DNA
<213> ORGANISM: Homo sapiens

<400> SEQUENCE: 31
gcagaggttt cagtgaccca agatcgcacc                                     30

<210> SEQ ID NO 32
<211> LENGTH: 45
<212> TYPE: DNA
<213> ORGANISM: Homo sapiens

<400> SEQUENCE: 32
aacctgggag gcagaggttt cagtgaccca agatcgcacc attgc                    45

<210> SEQ ID NO 33
<211> LENGTH: 50
<212> TYPE: DNA
<213> ORGANISM: Homo sapiens

<400> SEQUENCE: 33
tgtaatccca gctactcagg aggctgaggc aggagaattg cttgaacccg                50

```
<210> SEQ ID NO 34
<211> LENGTH: 56
<212> TYPE: DNA
<213> ORGANISM: Homo sapiens

<400> SEQUENCE: 34
tgcctgtaat cccagctact caggaggctg aggcaggaga attgcttgaa cccggg        56

<210> SEQ ID NO 35
<211> LENGTH: 66
<212> TYPE: DNA
<213> ORGANISM: Homo sapiens

<400> SEQUENCE: 35
caggtgcctg taatcccagc tactcaggag gctgaggcag gagaattgct tgaacccggg    60
aggcgg                                                               66

<210> SEQ ID NO 36
<211> LENGTH: 86
<212> TYPE: DNA
<213> ORGANISM: Homo sapiens

<400> SEQUENCE: 36
ggcgtggtgg caggtgcctg taatcccagc tactcaggag gctgaggcag gagaattgct    60
tgaacccggg aggcggaggt tgcggt                                         86

<210> SEQ ID NO 37
<211> LENGTH: 58
<212> TYPE: DNA
<213> ORGANISM: Homo sapiens

<400> SEQUENCE: 37
tgggaggcta aggcaggaga atcgcttgaa cctggaggca gaggttgcag tgagccca      58

<210> SEQ ID NO 38
<211> LENGTH: 64
<212> TYPE: DNA
<213> ORGANISM: Homo sapiens

<400> SEQUENCE: 38
tcttgggagg ctaaggcagg agaatcgctt gaacctggag gcagaggttg cagtgagccc    60
agat                                                                 64

<210> SEQ ID NO 39
<211> LENGTH: 74
<212> TYPE: DNA
<213> ORGANISM: Homo sapiens

<400> SEQUENCE: 39
catcttcttg ggaggctaag gcaggagaat cgcttgaacc tggaggcaga ggttgcagtg    60
agcccagatc gcac                                                      74

<210> SEQ ID NO 40
<211> LENGTH: 94
<212> TYPE: DNA
<213> ORGANISM: Homo sapiens

<400> SEQUENCE: 40
cctataatcc catcttcttg ggaggctaag gcaggagaat cgcttgaacc tggaggcaga    60
ggttgcagtg agcccagatc gcaccactac gctc                                94
```

```
<210> SEQ ID NO 41
<211> LENGTH: 154
<212> TYPE: DNA
<213> ORGANISM: Homo sapiens

<400> SEQUENCE: 41
caaaaattag ccaaggggtg gtggtgggca cctataatcc catcttcttg ggaggctaag      60
gcaggagaat cgcttgaacc tggaggcaga ggttgcagtg agcccagatc gcaccactac     120
gctccagcct aggtgacaga gagagactcc gtct                                 154

<210> SEQ ID NO 42
<211> LENGTH: 15
<212> TYPE: DNA
<213> ORGANISM: Homo sapiens

<400> SEQUENCE: 42
aggcaagatc tagat                                                       15

<210> SEQ ID NO 43
<211> LENGTH: 18
<212> TYPE: DNA
<213> ORGANISM: Homo sapiens

<400> SEQUENCE: 43
ccaaggcaag atctagat                                                    18

<210> SEQ ID NO 44
<211> LENGTH: 21
<212> TYPE: DNA
<213> ORGANISM: Homo sapiens

<400> SEQUENCE: 44
ttgccaaggc aagatctaga t                                                21

<210> SEQ ID NO 45
<211> LENGTH: 14
<212> TYPE: DNA
<213> ORGANISM: Homo sapiens

<400> SEQUENCE: 45
aaactcagca tcta                                                        14

<210> SEQ ID NO 46
<211> LENGTH: 17
<212> TYPE: DNA
<213> ORGANISM: Homo sapiens

<400> SEQUENCE: 46
cacaaactca gcatcta                                                     17

<210> SEQ ID NO 47
<211> LENGTH: 20
<212> TYPE: DNA
<213> ORGANISM: Homo sapiens

<400> SEQUENCE: 47
acacacaaac tcagcatcta                                                  20

<210> SEQ ID NO 48
<211> LENGTH: 12
<212> TYPE: DNA
<213> ORGANISM: Homo sapiens
```

```
<400> SEQUENCE: 48
gatctagatg ct                                                    12

<210> SEQ ID NO 49
<211> LENGTH: 15
<212> TYPE: DNA
<213> ORGANISM: Homo sapiens

<400> SEQUENCE: 49
caagatctag atgct                                                 15

<210> SEQ ID NO 50
<211> LENGTH: 15
<212> TYPE: DNA
<213> ORGANISM: Homo sapiens

<400> SEQUENCE: 50
gatctagatg ctgag                                                 15

<210> SEQ ID NO 51
<211> LENGTH: 18
<212> TYPE: DNA
<213> ORGANISM: Homo sapiens

<400> SEQUENCE: 51
caagatctag atgctgag                                              18

<210> SEQ ID NO 52
<211> LENGTH: 24
<212> TYPE: DNA
<213> ORGANISM: Homo sapiens

<400> SEQUENCE: 52
aggcaagatc tagatgctga gttt                                       24

<210> SEQ ID NO 53
<211> LENGTH: 12
<212> TYPE: DNA
<213> ORGANISM: Homo sapiens

<400> SEQUENCE: 53
ggagtggaaa ga                                                    12

<210> SEQ ID NO 54
<211> LENGTH: 15
<212> TYPE: DNA
<213> ORGANISM: Homo sapiens

<400> SEQUENCE: 54
ccaggagtgg aaaga                                                 15

<210> SEQ ID NO 55
<211> LENGTH: 17
<212> TYPE: DNA
<213> ORGANISM: Homo sapiens

<400> SEQUENCE: 55
aaccaggagt ggaaaga                                               17

<210> SEQ ID NO 56
<211> LENGTH: 18
<212> TYPE: DNA
```

<213> ORGANISM: Homo sapiens

<400> SEQUENCE: 56
gaaccaggag tggaaaga                                            18

<210> SEQ ID NO 57
<211> LENGTH: 21
<212> TYPE: DNA
<213> ORGANISM: Homo sapiens

<400> SEQUENCE: 57
aaagaaccag gagtggaaag a                                        21

<210> SEQ ID NO 58
<211> LENGTH: 12
<212> TYPE: DNA
<213> ORGANISM: Homo sapiens

<400> SEQUENCE: 58
tacacgagca tc                                                  12

<210> SEQ ID NO 59
<211> LENGTH: 14
<212> TYPE: DNA
<213> ORGANISM: Homo sapiens

<400> SEQUENCE: 59
tgtacacgag catc                                                14

<210> SEQ ID NO 60
<211> LENGTH: 16
<212> TYPE: DNA
<213> ORGANISM: Homo sapiens

<400> SEQUENCE: 60
cttgtacacg agcatc                                              16

<210> SEQ ID NO 61
<211> LENGTH: 18
<212> TYPE: DNA
<213> ORGANISM: Homo sapiens

<400> SEQUENCE: 61
aacttgtaca cgagcatc                                            18

<210> SEQ ID NO 62
<211> LENGTH: 20
<212> TYPE: DNA
<213> ORGANISM: Homo sapiens

<400> SEQUENCE: 62
caaacttgta cacgagcatc                                          20

<210> SEQ ID NO 63
<211> LENGTH: 22
<212> TYPE: DNA
<213> ORGANISM: Homo sapiens

<400> SEQUENCE: 63
ggcaaacttg tacacgagca tc                                       22

<210> SEQ ID NO 64
<211> LENGTH: 15

```
<212> TYPE: DNA
<213> ORGANISM: Homo sapiens

<400> SEQUENCE: 64
gtggaaagat gctcg                                              15

<210> SEQ ID NO 65
<211> LENGTH: 21
<212> TYPE: DNA
<213> ORGANISM: Homo sapiens

<400> SEQUENCE: 65
ggagtggaaa gatgctcgtg t                                       21

<210> SEQ ID NO 66
<211> LENGTH: 27
<212> TYPE: DNA
<213> ORGANISM: Homo sapiens

<400> SEQUENCE: 66
ccaggagtgg aaagatgctc gtgtaca                                 27

<210> SEQ ID NO 67
<211> LENGTH: 15
<212> TYPE: DNA
<213> ORGANISM: Homo sapiens

<400> SEQUENCE: 67
gaaaaagatc ttcag                                              15

<210> SEQ ID NO 68
<211> LENGTH: 21
<212> TYPE: DNA
<213> ORGANISM: Homo sapiens

<400> SEQUENCE: 68
tcagaaaaag atcttcaggg g                                       21

<210> SEQ ID NO 69
<211> LENGTH: 27
<212> TYPE: DNA
<213> ORGANISM: Homo sapiens

<400> SEQUENCE: 69
acatcagaaa aagatcttca ggggct                                  27

<210> SEQ ID NO 70
<211> LENGTH: 14
<212> TYPE: DNA
<213> ORGANISM: Homo sapiens

<400> SEQUENCE: 70
acatcagaaa aaga                                               14

<210> SEQ ID NO 71
<211> LENGTH: 17
<212> TYPE: DNA
<213> ORGANISM: Homo sapiens

<400> SEQUENCE: 71
agcacatcag aaaaaga                                            17

<210> SEQ ID NO 72
```

```
<211> LENGTH: 20
<212> TYPE: DNA
<213> ORGANISM: Homo sapiens

<400> SEQUENCE: 72
caaagcacat cagaaaaaga                                              20

<210> SEQ ID NO 73
<211> LENGTH: 23
<212> TYPE: DNA
<213> ORGANISM: Homo sapiens

<400> SEQUENCE: 73
gaacaaagca catcagaaaa aga                                          23

<210> SEQ ID NO 74
<211> LENGTH: 26
<212> TYPE: DNA
<213> ORGANISM: Homo sapiens

<400> SEQUENCE: 74
ccagaacaaa gcacatcaga aaaaga                                       26

<210> SEQ ID NO 75
<211> LENGTH: 15
<212> TYPE: DNA
<213> ORGANISM: Homo sapiens

<400> SEQUENCE: 75 agcccccctga agatc                                                  15

<210> SEQ ID NO 76
<211> LENGTH: 18
<212> TYPE: DNA
<213> ORGANISM: Homo sapiens

<400> SEQUENCE: 76
tctagccccc tgaagatc                                                18

<210> SEQ ID NO 77
<211> LENGTH: 21
<212> TYPE: DNA
<213> ORGANISM: Homo sapiens

<400> SEQUENCE: 77
atttctagcc ccctgaagat c                                            21

<210> SEQ ID NO 78
<211> LENGTH: 24
<212> TYPE: DNA
<213> ORGANISM: Homo sapiens

<400> SEQUENCE: 78
cagatttcta gcccccctgaa gatc                                        24

<210> SEQ ID NO 79
<211> LENGTH: 27
<212> TYPE: DNA
<213> ORGANISM: Homo sapiens

<400> SEQUENCE: 79
caacagattt ctagcccccct gaagatc                                     27
```

-continued

```
<210> SEQ ID NO 80
<211> LENGTH: 39
<212> TYPE: DNA
<213> ORGANISM: Homo sapiens

<400> SEQUENCE: 80
tgctcgtgta caagtttgcc agaaaacacc acatcactt                              39

<210> SEQ ID NO 81
<211> LENGTH: 120
<212> TYPE: DNA
<213> ORGANISM: Homo sapiens

<400> SEQUENCE: 81
ataagtgact cttctgccct tgaggacctg cgaaatccag aacaaagcac atcagaaaaa      60
gatcttcagg gggctagaaa tctgttgcta tgggcccttc accaacatgc ccacagatca    120

<210> SEQ ID NO 82
<211> LENGTH: 210
<212> TYPE: DNA
<213> ORGANISM: Homo sapiens

<400> SEQUENCE: 82
gatcttcagg gggctagaaa tctgttgcta tgggcccttc accaacatgc ccacagatca     60
actggaatgg atggtacagc tgtgtggtgc ttctgtggtg aaggagcttt catcattcac    120
ccttggcaca ggtgtccacc caattgtggt tgtgcagcca gatgcctgga cagaggacaa    180
tggcttccat gcaattgggc agatgtgtga                                      210

<210> SEQ ID NO 83
<211> LENGTH: 8
<212> TYPE: PRT
<213> ORGANISM: Homo sapiens

<400> SEQUENCE: 83

Arg Gln Asp Leu Asp Ala Glu Phe
1               5

<210> SEQ ID NO 84
<211> LENGTH: 10
<212> TYPE: PRT
<213> ORGANISM: Homo sapiens

<400> SEQUENCE: 84

Pro Arg Gln Asp Leu Asp Ala Glu Phe Val
1               5                   10

<210> SEQ ID NO 85
<211> LENGTH: 12
<212> TYPE: PRT
<213> ORGANISM: Homo sapiens

<400> SEQUENCE: 85

Leu Pro Arg Gln Asp Leu Asp Ala Glu Phe Val Cys
1               5                   10

<210> SEQ ID NO 86
<211> LENGTH: 14
<212> TYPE: PRT
<213> ORGANISM: Homo sapiens

<400> SEQUENCE: 86

Tyr Leu Pro Arg Gln Asp Leu Asp Ala Glu Phe Val Cys Glu
```

-continued

```
1               5                   10
```

<210> SEQ ID NO 87
<211> LENGTH: 16
<212> TYPE: PRT
<213> ORGANISM: Homo sapiens

<400> SEQUENCE: 87

```
Ser Tyr Leu Pro Arg Gln Asp Leu Asp Ala Glu Phe Val Cys Glu Arg
1               5                   10                  15
```

<210> SEQ ID NO 88
<211> LENGTH: 9
<212> TYPE: PRT
<213> ORGANISM: Homo sapiens

<400> SEQUENCE: 88

```
Pro Gly Val Glu Arg Cys Ser Cys Thr
1               5
```

<210> SEQ ID NO 89
<211> LENGTH: 11
<212> TYPE: PRT
<213> ORGANISM: Homo sapiens

<400> SEQUENCE: 89

```
Glu Pro Gly Val Glu Arg Cys Ser Cys Thr Ser
1               5                   10
```

<210> SEQ ID NO 90
<211> LENGTH: 7
<212> TYPE: PRT
<213> ORGANISM: Homo sapiens

<400> SEQUENCE: 90

```
Pro Glu Asn Thr Thr Ser Leu
1               5
```

<210> SEQ ID NO 91
<211> LENGTH: 9
<212> TYPE: PRT
<213> ORGANISM: Homo sapiens

<400> SEQUENCE: 91

```
Thr Ser Glu Lys Asp Leu Gln Gly Ala
1               5
```

<210> SEQ ID NO 92
<211> LENGTH: 11
<212> TYPE: PRT
<213> ORGANISM: Homo sapiens

<400> SEQUENCE: 92

```
Ser Thr Ser Glu Lys Asp Leu Gln Gly Ala Arg
1               5                   10
```

<210> SEQ ID NO 93
<211> LENGTH: 40
<212> TYPE: PRT
<213> ORGANISM: Homo sapiens

<400> SEQUENCE: 93

```
Ile Ser Asp Ser Ser Ala Leu Glu Asp Leu Arg Asn Pro Glu Gln Ser
1               5                   10                  15
```

-continued

```
Thr Ser Glu Lys Asp Leu Gln Gly Ala Arg Asn Leu Leu Leu Trp Ala
            20                  25                  30

Leu His Gln His Ala His Arg Ser
        35              40
```